United States Patent [19]

Saeki et al.

[11] Patent Number: 5,612,204
[45] Date of Patent: Mar. 18, 1997

[54] BIOLOGICAL DEGRADATIVE TREATMENT OF CHLORINE SUBSTITUTED ETHYLENE

[75] Inventors: Hisashi Saeki; Akira Miura, both of Saitama, Japan

[73] Assignee: Japan Energy Corporation, Tokyo, Japan

[21] Appl. No.: 499,215

[22] Filed: Jul. 7, 1995

[30] Foreign Application Priority Data

Jul. 8, 1994 [JP] Japan .................................. 6-179689

[51] Int. Cl.$^6$ .............................. C12P 7/00; C12N 9/00; C07H 17/00
[52] U.S. Cl. .......................... 435/132; 536/23.7; 435/183
[58] Field of Search .......................... 536/23.7; 435/132, 435/183

[56] References Cited

U.S. PATENT DOCUMENTS

| | | | |
|---|---|---|---|
| 4,956,284 | 9/1990 | Phillips et al. | 435/123 |
| 4,959,315 | 9/1990 | Nelson et al. | 435/167 |
| 5,079,166 | 1/1992 | Winter et al. | 435/262 |
| 5,376,539 | 12/1994 | Furuhashi et al. | 435/117 |
| 5,380,654 | 1/1995 | Furuhashi et al. | 435/117 |
| 5,441,885 | 8/1995 | Goldberg et al. | 435/252.34 |
| 5,441,887 | 8/1995 | Hanson et al. | 435/262.5 |

OTHER PUBLICATIONS

Van Ginkel et al 1987 Appl. Environ. Microbiol. 53:2903–2907.
Miura et al 1995 Biosci Biotech Biochem 59:853–859.
Hartmans et al 1991 J Gene Microbiol 137:2555–2560.
Saeki et al 1994 J Ferment. Bioeng. 78:399–406.
Hartmans et al 1992 Appl. Environ. Microbiol. 58:1220–1226.
Ensign et al 1992 Appl. Environ. Microbiol. 58:3038–3046.
Biosci. Biotech. Biochem., 56(3)486–489, 1992, Toshiaki Nakajima et al. "Novel Metabolite of Traichloroethylene in a Methanotrophic Bacterium".
Biotechnology vol. 7, Mar. 1989, R. Winter et al, "Efficient Degradation of Trichloroethylene by a Recombinant *Escherichia Coli*".

*Primary Examiner*—Robert A. Wax
*Assistant Examiner*—K. Cochrane Carlson
*Attorney, Agent, or Firm*—Sughrue, Mion, Zinn, Macpeak & Seas

[57] ABSTRACT

A method for biologically degradative-treating a chlorine-substituted ethylene comprising culturing a microorganism capable of producing an alkene monooxygenase in a medium containing a chlorine-substituted ethylene having 1 to 3 chlorine atoms and wherein said chlorine-substituted ethylene is oxidized to a corresponding epoxide. Chlorine-substituted ethylenes are degraded at high rate and efficiency by the oxidation using microorganisms.

9 Claims, 5 Drawing Sheets

EFFECT OF TCE CONCENTRATION ON TCE DEGRADATION RATE

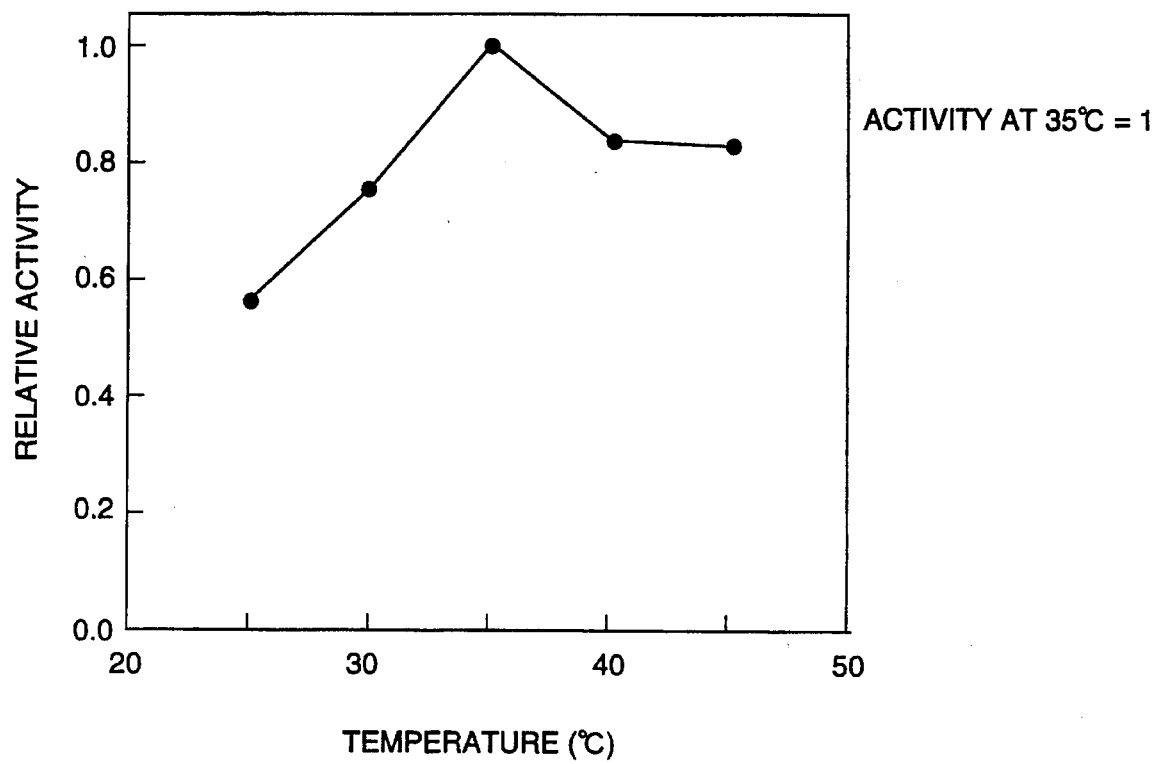

SUBSTRATE SPECIFICITY

BIOLOGICAL DEGRADATIVE TREATMENT OF CHLORINE SUBSTITUTED ETHYLENE

FIELD OF THE INVENTION

This invention relates to a biological method for degrading a chlorine-substituted ethylene. More particularly, it relates to a method for degrading a chlorine-substituted ethylene, such as trichloroethylene, by biological oxidation comprising culturing (a) a microorganism capable of producing an alkene monooxygenase or (b) a microorganism capable of growing in a medium containing an alkene as a sole carbon source, in a medium containing the chlorine-substituted ethylene to be treated thereby wherein the microorganism acts on the chlorine-substituted ethylene to decompose same.

BACKGROUND OF THE INVENTION

Halogen-substituted aliphatic hydrocarbons, especially chlorine-substituted compounds having 1 or 2 carbon atoms, have been widely used as a solvent in detergents because of their high dissolving power for organic substances such as fats and oils. For example, trichloroethylene, a typical chlorine-substituted ethylene, is sparingly water soluble and highly volatile and has been used chiefly as a solvent for dry cleaning or for degreasing in the electromachinery industry or the semiconductor industry. Trichloroethylene exhibits an inhibitory action on the central nervous system and an anesthetic action similar to chloroform, and has been reported to be a mutagen (teratogen) and carcinogen. Because of its toxicity, trichloroethylene, should be collected and recycled. Should trichloroethylene be present in waste water, it would accumulate in soil or in groundwater since it is not easily degraded in nature and is sparingly soluble in water. To remedy trichloroethylene pollution, it is recovered physically, for example, by a method comprising exposing pumped groundwater to air and collecting the volatized trichloroethylene from the air, by a method in which pumped groundwater is treated with activated carbon, or by a method of adsorbing and removing a soil gas under reduced pressure. The thus recovered trichloroethylene is then decomposed by combustion or by a photochemical means using a catalyst.

It has been found that some anaerobic bacteria living in soil produce, from trichloroethylene, vinyl chloride (chloroethylene) or dichloroethylene which are more mutagenic (teratogenic) or carcinogenic than trichloroethylene [see E. J. Bouwer and P. L. McCarty, *Appl. Environ. Microbiol.*, 45, 1286 (1983), T. M. Vogel, C. S. Criddle and P. L. McCarty, *Environ. Sci. Technol.*, 21, 722 (1987) and *Appl. Environ. Microbiol.*, 49, 1080 (1985)]. Thus, the immediate degradative treatment of trichloroethylene pollution is of increasing demand. Great expectations have recently been held for use of microorganisms for the purpose of degrading trichloroethylene which has accumulated in groundwater and is diffused over a wide area in a relatively low concentration.

Besides the anaerobic bacteria capable of producing vinyl chloride (chloroethylene) or dichloroethylene from trichloroethylene, it has been reported that some aerobic bacteria are capable of degrading halogen-substituted aliphatic hydrocarbons. With respect to the biological degradation of trichloroethylene using aerobic microorganisms, use of microorganisms capable of producing an enzyme catalyzing oxidation of ammonia, methane or a methyl group, i.e., an enzyme for oxidizing an atomic group containing no double bond, has been reported. Such microorganisms include toluene-assimilating microorganisms capable of producing toluene dioxygenase [see G. J. Zylstra, L. P. Wackett and D. T. Gibson, *Appl. Environ. Microbiol.*, 55, 3162 (1989)], toluene-assimilating microorganisms capable of producing toluene monooxygenase [see R. B. Winter, K-M. Yen and B. D. Ensley, *Bio/Technol7*,282 (1989)], methane-assimilating microorganisms capable of producing methane monooxygenase [see R. Oldenhuis, R. L. J. M. Vink, D. B. Janssen, and B. Witholt, *Appl. Environ. Microbiol.*, 55, 2819 (1989)], and ammonia-assimilating microorganisms capable of producing ammonia monooxygenase [see T. Vannelli, M. Logan, D. M. Arciero, and A. B. Hooper, *Appl. Environ. Microbiol.*, 56, 1169 (1990)]. Aside from these enzymes for converting a hydrogen atom of hydrocarbons to a hydroxyl group, biological technology for degrading trichloroethylene utilizing other hydrocarbon oxidizing enzymes has not yet been established. In particular, development of a biological method suitable for degrading trichloroethylene at high efficiency has been demanded.

In addition, it has been demanded that a method for biologically degrading not only trichloroethylene but other chlorine-substituted ethylenes, such as vinyl chloride (chloroethylene) and dichloroethylene, which are produced from trichloroethylene by the action of anaerobic bacteria be developed.

SUMMARY OF THE INVENTION

An object of the present invention is to provide a novel method for biologically treating a chlorine-substituted ethylene, such as trichloroethylene, to degrade it at a high efficiency, thereby solving the above-described problems. In particular, the object is to provide a method for degrading a chlorine-substituted ethylene efficiently through an oxidation reaction of an enzyme catalyzing oxidation of non-aromatic hydrocarbons in place of an enzyme catalyzing oxidation of aromatic hydrocarbons, that is, by using a microorganism capable of producing an enzyme catalyzing oxidation of a non-aromatic hydrocarbon or a microorganism capable of assimilating a non-aromatic hydrocarbon.

As a result of extensive studies, the present inventors have found that a chlorine-substituted ethylene, such as trichloroethylene, is biologically oxidized to a corresponding epoxide, such as trichloroethylene oxide, by the action of a microorganism which assimilates an alkene (a non-aromatic hydrocarbon) or a microorganism capable of producing an alkene monooxygenase catalyzing oxidation of an alkene to a corresponding epoxide. The present invention has been reached based on this finding.

The present invention provides a method for biologically degradative-treating a chlorine-substituted ethylene as embodied in embodiments (1) through (7) described below.

(1) A method for biologically degradative-treating a chlorine-substituted ethylene comprising culturing a microorganism capable of producing an alkene monooxygenase in a medium containing a chlorine-substituted ethylene having 1 to 3 chlorine atoms in the presence of a chlorine-substituted ethylene to biologically oxidize the chlorine-substituted ethylene to a corresponding epoxide.

(2) A method for biologically degradative-treating a chlorine-substituted ethylene comprising culturing a microorganism capable of growing in a medium containing an alkene as a sole carbon source, in a medium containing a chlorine-substituted ethylene having 1 to 3 chlorine atoms wherein the microorganism acts on the chlorine-substituted ethylene to biologically oxidize the chlorine-substituted ethylene to a corresponding epoxide.

(3) A method for biologically degradative-treating a chlorine-substituted ethylene according to (1) above, wherein the microorganism is a transformant having a plasmid vector containing DNA encoding an alkene monooxygenase.

(4) A method for biologically degradative-treating a chlorine-substituted ethylene according to any of (1) to (3) above, wherein the microorganism belongs to a genus selected from the group consisting of Nocardia, Rhodococcus, Xanthobacter, and Mycobacterium.

(5) A method for biologically degradative-treating a chlorine-substituted ethylene according to any of (1), (2) and (4) above, wherein the microorganism is *Nocardia corallina* B-276 (FERM P-4094; FERM BP-5124; ATCC 31338).

(6) A method for biologically degradative-treating a chlorine-substituted ethylene according to (3) or (4) above, wherein the gene DNA encoding an alkene monooxygenase is obtained from *Nocardia corallina* B-276 (FERM P-4094; FERM BP-5124; ATCC 31338).

(7) A method for biologically degradative-treating a chlorine-substituted ethylene according to (3) or (6) above, wherein the transformed microorganism is an *Escherichia coli*.

(8) A DNA fragment containing a gene encoding an alkene monooxygenase obtained from *Nocardia corallina* B-276 (FERM P-4094; FERM BP-5124; ATCC 31338).

(9) A transformant microorganism carrying an expression vector containing the DNA fragment encoding an alkene monooxygenase obtained from *Nocardia corallina* B-276 (FERM P-4094; FERM BP-5124; ATCC 31338).

BRIEF DESCRIPTION OF THE DRAWINGS

FIG. 4 is a graph showing the temperature dependence of reaction rate in the reaction system using *Nocardia corallina* B-276 (FERM P-4094; FERM BP-5124; ATCC 31338).

DETAILED DESCRIPTION OF THE INVENTION

Figure 1:
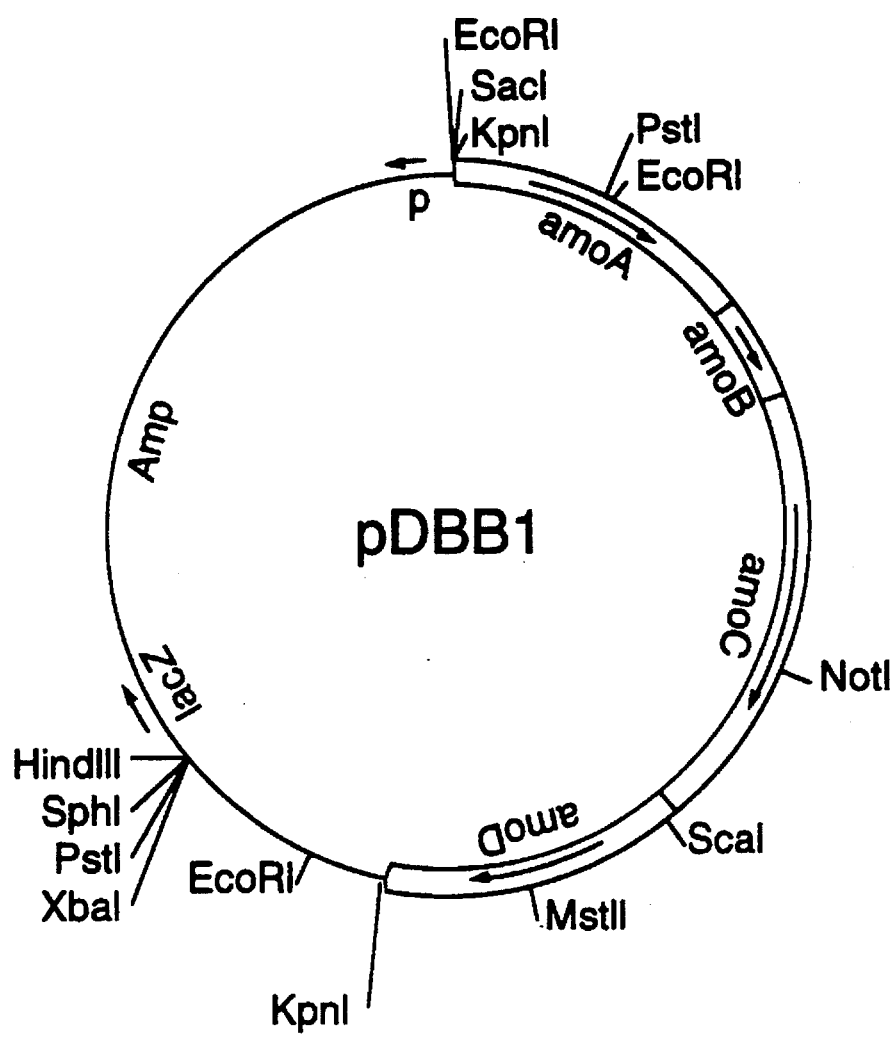
FIG. 1 is a restriction enzyme map of plasmid vector pDBB1 held in *E. coli* JM109 (pDBB-1) (FERM BP-4250), in which the amoABCD gene and relevant restriction sites are shown.

The chlorine-substituted ethylene having 1 to 3 chlorine atoms which can be degraded by the method of the present invention includes trichloroethylene, 1,1-dichloroethylene, cis-1,2-dichloroethylene, trans-1,2-dichloroethylene, and vinyl chloride (chloroethylene). The epoxide produced from the chlorine-substituted ethylene by the method of the present invention is unstable and ring-opened rapidly on addition of water present in quantity in the culture medium and is thereby converted into a chlorine-substituted ethanediol. In the final stage, the chlorine-substituted ethanediol undergoes further biological metabolism (decomposition) or chemical displacement of the chlorine atom(s) with a hydroxyl group(s).

Of the microorganisms which can be used in the present invention, those capable of growing in a medium containing an alkene as a sole carbon source can be isolated by cultivating microorganisms collected from, for example, soil in a medium containing propylene as a sole carbon source. Microorganisms which convert propylene into propene oxide are preferred. Microorganisms belonging to the genus Nocardia, Rhodococcus, Xanthobacter or Mycobacterium which have been reported as being capable of enzymatically producing propene oxide from propylene are particularly preferred for their high capability of oxidizing propylene to propene oxide. Illustrative examples of the microorganisms included under the above category are given, e.g., in C. G. van Ginkel, H. G. J. Welten, and J. A. M. de Bont, *Appl. Environ Microbiol.*, 53, 2903 (1987).

Microorganisms of another type to be used in the present invention are those capable of producing an alkene monooxygenase which is an oxygenase participating in the initial stage of alkene metabolism, that is, microorganisms capable of producing an alkene monooxygenase catalyzing conversion of an alkene into a corresponding epoxide. For example, microorganisms capable of producing an alkene monooxygenase can be isolated from, for example, soil as microorganisms converting propylene as an alkene into a corresponding epoxide. Suitable microorganisms of this type include those belonging to the genus Nocardia, Rhodococcus, Xanthobacter or Mycobacterium and capable of converting an alkene having a carbon-carbon double bond at the end position thereof into a corresponding 1,2-epoxide. Illustrative examples of such microorganisms are described in C. G. van Ginkel, H. G. J. Welten, and J. A. M. de Bont, *Appl. Environ. Microbiol.*, 53, 2903 (1987).

Examples of suitable bacteria belonging to the genus Rhodococcus are, for example, species *Rhodococcus rhodochrous* (examples of this species are deposited at the American Type Culture Collection under accession numbers ATCC 29675, ATCC 29670 and ATCC 29672, which are listed in U.S. Pat. No. 5,380,654 and U.S. Pat. No. 5,376,539). Other examples of suitable bacteria belonging to the genus Rhodococcus are strains Rhodococcus sp. ATCC 29673 or Rhodococcus sp. ATCC 29674, which are also listed in U.S. Pat. No. 5,380,654 and U.S. Pat. No. 5,376,539. Some other examples of bacteria having alkene monooxygenase are Mycobacterium strain L1 described in *Biotechnol. lett.*, 7, 383–388 (1985) or in *J. Gen. Microbiol*, 137, 2555–2560 (1991), species *Mycobacterium rhodochrous* (an example of this species is deposited at the NCIB under the accession number of 703, which is described in U.S. Pat. No. 4,956,284), Xanthobacter strain Py2 described in *Appl. Environ. Microbiol.*, 58, 3038 (1992), and so on.

Microorganisms to which alkene monooxygenase-producing capability has been introduced by genetic engineering are also suitable in the present invention. Such transformant microorganisms capable of producing an alkene monooxygenase can be obtained by integrating an isolated DNA encoding an alkene monooxygenase originating in a naturally-occurring alkene monooxygenase-producing microorganism, or the like into a plasmid by known gene recombination techniques to obtain a recombinant plasmid vector and introducing the recombinant vector into a host microorganism.

Among microorganisms capable of growing in a medium containing an alkene as a sole carbon source, when the microorganisms are grown with carbohydrates such as glucose as a carbon source, those capable of metabolizing an alkene such as propylene can be used much more suitably. Among microorganisms capable of producing an alkene monooxygenase, when the microorganisms are grown or cultivated with carbohydrates such as glucose as a carbon source, those capable of maintaining the alkene monooxygenase as an effective enzyme can be also used much more suitably.

Particularly preferred microorganisms include *Nocardia corallina* B-276 (FERM P-4094; FERM BP-5124; ATCC 31338), disclosed in Japanese Patent Application No. Hei-5-105171, i.e., JP-A-6-292571 (the term "JP-A" as used herein means an "unexamined published Japanese patent application"), filed by the present inventors; and *E. coli* transformants capable of producing an alkene monooxygenase, obtained by transformation of *E. coli* with a plasmid vector of *E. coli* origin into which gene DNA encoding an alkene monooxygenase produced by *Nocardia corallina* B-276 (amoABCD gene) has been integrated, e.g., *E. coli* JM109, pDBB-1 strain (FERM BP-4250). The above-mentioned strains, Nocardia corallina B-276 (FERM P-4094; FERM BP-5124; ATCC 31338) and *E. coli* JM109, pDBB-1 strain (FERM BP-4250) are deposited at the National Institute of Bioscience & Human Technology under deposit numbers FERM P-4094 and FERM BP-4250, respectively. The original deposit of the former strain was transferred to the deposit under the Budapest Treaty and received a deposit number FERM BP-5124. The former strain also is deposited at the American Type Culture Collection under accession number ATCC 31338.

In general, the alkene monooxygenase is a multicomponent enzyme composed of monooxygenase units and a reductase unit, that was reported in *J. Gen. Microbiol.*, 137, 2555–2560 (1991). The genes encoding the multicomponent enzyme such as the alkene monooxygenase can be isolated by cloning procedures described in BIO/TECHNOLOGY Vol. 7, 282 (1989) and references therein.

Partially identified peptide sequences of the units of multicomponent enzyme are utilized to produce cloning probes corresponding to the peptide sequences. In usual, cloning procedures described in Genetic Manipulation of Streptomyces. A laboratory manual, John Innes Foundation, Norwich, England (1985) can be applied successfully. The isolation of the genes encoding an alkene monooxygenase from *Nocardia corallina* B-276 presented in JP-A-6-292571 was made using the above-mentioned cloning procedures with little modification.

The above-mentioned transformant microorganisms capable of producing an alkene monooxygenase, which is obtained by integrating an isolated DNA encoding an alkene monooxygenase originating in a naturally-occurring alkene monooxygenase-producing microorganism, or the like into a plasmid by gene recombination techniques to obtain a recombinant plasmid vector and introducing that vector into a host microorganism, are not limited to those prepared by using *E. coli* as a host microorganism but also include those prepared by using a plasmid originating in a Nocardiform bacterium of genus Nocardia, Rhodococcus, etc. and by introducing such a plasmid vector having integrated therein gene DNA encoding a foreign alkene monooxygenase into a Nocardiform bacterium as a host microorganism. The plasmid of Nocardiform or Coryneform bacterium origin which can be used in the construction of a vector for the use of recombinant DNA techniques in this group of bacteria and also in the close-related group includes plasmid pNC500 (see JP-A-5-244953) and plasmid pNC903 (see Japanese Patent Application No. Hei-6-73795), both constructed by the present inventors. Host-vector systems (genetic recombination systems) developed for this group of bacteria such as genus of *Rhodococcus, Nocardia*, or the like (see *J. General Microbiology*, 138, 1003–1010 (1992)) are effective to transform these bacteria and useful for expression of the cloned genes. Transformation is carried out very often by the methods of electoporation (see *Appl. Environ. Microbiol.*, 56, 2818–2825 (1990)) or of Vogt Singer & Finnetry (see *J. Bacteriology*, 170, 368–645 (1988)). The expression vector containing the cloned genes encoding an alkene monooxygenase enzyme can be usually constructed as an *E. coli*-host microorganism shuttle plasmid by combining fragments of at least a part of plasmid from *E. coli*, of at least a part of plasmid from Nocardiform or Coryneform bacterium and of at least a part of the cloned genes.

The alkene monooxygenase to be used in the above-mentioned transformation preferably includes the one produced by *Nocardia corallina* B-276 (FERM P-4094, FERM BP-5124; ATCC 31338). This enzyme is composed of four protein subunits; amoA and amoC corresponding to a small subunit and a large subunit, respectively, of epoxidase which adds oxygen to an alkene to form an epoxide, amoD serving as a reductase for transmitting an electron from coenzyme NADH to the epoxidase, and amoB called a coupling protein which holds these portions in a complex enzyme unit.

The amino acid sequence of each of amoA, amoB, amoC, and amoD is coded as a continuous gene cluster in the amoABCD gene whose sequence is shown in SEQ ID NO:1. The amino acid sequences are shown in SEQ ID NO:1 at corresponding positions to the codons of the amoABCD gene (cf. Japanese Patent Application No. Hei-5-105171, i.e., JP-A-6-292571). A plasmid vector (pDBB1, see FIG. 1) obtained by integrating this preferred amoABCD gene into a commercially available plasmid of *E. coli* origin (pUC18, purchased from Takara Shuzo Co., Ltd.) is maintained in *E. coli* JM109, pDBB-1 strain (FERM BP-4250). Other transformant strains obtained by introducing plasmid vector pDBB1 into various other strains of *E. coli* can preferably be used as alkene monooxygenase-producing microorganisms.

The present invention also provides a DNA fragment containing a gene encoding alkene monooxygenase obtained from *Nocardia corallina* B-276 (FERM P-4094; FERM BP-5124; ATCC 31338) and a transformant microorganism carrying an expression vector containing such a DNA fragment. Preferable examples of the DNA fragment containing a gene encoding alkene monooxygenase obtained from *Nocardia corallina* B-276 (FERM P-4094; FERM BP-5124; ATCC 31338) include a DNA fragment comprising a nucleotide sequence corresponding to the open reading frame shown in SEQ ID NO:1 and a DNA fragment comprising nucleotide sequences respectively encoding amoA, amoB, amoC, and amoD. The above-described sequences may have deletions, additional bases, overlapping regions, replacements of the base taking the degeneracy of the codon into consideration, or the like as long as a transformant carrying an expression vector containing the DNA fragment is capable of expressing proper amoA, amoB, amoC, and amoD.

In the present invention, either a microorganism which can grow in a medium containing an alkene as a sole carbon source or an alkene monooxygenase-producing microorganism is cultured in a medium containing a chlorine-substituted ethylene having 1 to 3 chlorine atoms whereby the chlorine-substituted ethylene is oxidized by the action of the microorganism. The cultivation is preferably carried out by aeration culture or aerobic culture. The alkene monooxygenase or an oxygenase participating in the alkene metabolism produced by the above microorganism can maintain a high enzyme activity level under aeration or aerobic conditions.

Growth of the microorganism can preferably be achieved by (a) a method in which microbial cells obtained by previous proliferation of the microorganism are cultured in a minimal medium containing a chlorine-substituted ethylene under an aerobic condition or (b) a method in which the microorganism is cultured under an aeration or aerobic condition in a nutrient medium containing carbon sources, nitrogen sources, inorganic salts and, if necessary, growth accelerators, to which a chlorine-substituted ethylene to be treated has been added. The culturing is conducted at a pH of 5 to 9, preferably 6 to 8, at a temperature of 20° to 50° C., preferably 25° to 45° C., for 1 to 6 days. The activity of the microbial cells on the chlorine-substituted ethylene can be maintained or enhanced by appropriately adding carbon sources, nitrogen sources or any other components advantageous for growth to the medium during cultivation.

In the method (a) in which the microorganism is previously proliferated, the medium to be used for previous proliferation comprises carbon sources having high cell proliferation action, such as carbohydrates (e.g., glucose, sucrose, molasses, starch hydrolyzate, and cellulose hydrolyzate) and hydrocarbons (e.g., propylene, ethylene, and butadiene); nitrogen sources, such as ammonium chloride, ammonium sulfate, ammonium phosphate, ammonium nitrate, urea, aqueous ammonia, amino acids, and other organic nitrogen compounds which can be assimilated; inorganic salts, such as potassium phosphate, sodium phosphate, magnesium sulfate, manganese sulfate, ferrous sulfate, ferric chloride, calcium chloride, and manganese chloride; and, if desired, growth accelerators, such as vitamins, yeast extract and corn steep liquor. The medium for proliferation is inoculated with the strain and cultured under an aerobic condition to proliferate the cells. A minimal medium containing a chlorine-substituted ethylene to be treated, such as trichloroethylene, is added to the thus obtained culture, a suspension of microbial cells separated from the culture, or immobilized microbial cells.

In the method (b) in which the microorganism is cultured in a nutrient medium containing a chlorine-substituted ethylene under an aeration or aerobic condition, the same nutrient medium used as a medium for cell proliferation in the method (a) is used, and a chlorine-substituted ethylene, e.g., trichloroethylene, is supplied to the medium for oxidation.

In either of method (a) or method (b), a prescribed amount of a chlorine-substituted ethylene may be added to the medium all at once at the beginning of cell growth or batchwise or continuously with the passage of growth. The batchwise addition may be intermittent. The chlorine-substituted ethylene, such as trichloroethylene, may be added to the medium in the form of liquid or as a mixture soluble or diffusible in water, or in the form of gas, for example, air containing the vapor of the chlorine-substituted ethylene, bubbled through the medium. The chlorine-substituted ethylene is preferably added to the medium in such an amount that the chlorine-substituted ethylene concentration in the medium does not exceed 1 mM. The biological reaction is preferably effected at a temperature between 30° and 40° C., particularly around 35° C.

The alkene monooxygenase-producing microorganism or the microorganism which can grow in a medium containing an alkene as a sole carbon source is capable of degrading not only trichloroethylene but chlorine-substituted ethylenes having at least one hydrogen atom and, further, an ethylene substituted with halogen other than fluorine and having at least one hydrogen atom. Accordingly, where the microorganism is used aerobically for the degradative treatment of trichloroethylene contained in contaminated groundwater, in case the groundwater should contain vinyl chloride (chloroethylene) or dichloroethylene which are produced from trichloroethylene by the action of anaerobic bacteria living in soil, the instant microorganism can degrade these chlorine-substituted ethylenes simultaneously. Moreover, the instant microorganisms do not suffer death or a reduction in physiological activity due to the high toxicity of vinyl chloride or dichloroethylene and is suitable for the long-term or continuous treatment of trichloroethylene contained in groundwater.

The present invention will now be illustrated in greater detail with reference to Examples, but it should be understood that the present invention is not deemed to be limited thereto.

EXAMPLE 1

In a 500 ml Sakaguchi's flask was put 100 ml of NBG medium (a liquid medium containing 10 g of Lab-Lemco powder (produced by Oxoid Co., Ltd.), 10 g of bacteriological peptone, 10 g of glucose, 5 g of sodium chloride, and water to make 1 l, adjusted to pH 7.5 with a 1N aqueous sodium hydroxide solution, steam sterilized by autoclaving at 120° C. for 15 minutes) and inoculated with three loopfuls of *Nocardia corallina* B-276 (FERM P-4094; FERM BP-5124; ATCC 31338) using a platinum loop, followed by shake culture at 30° C. for 96 hours for previous proliferation.

The resulting culture was centrifuged to collect the microbial cells, which were suspended in 50 ml of a minimal medium ($K_2HPO_4$ 1.74 g, $MgSO_4 \cdot 7H_2O$ 1.5 g, $FeSO_4 \cdot H_2O$ 0.05 g, deionized water 1 l; adjusted to pH 8.0) to prepare a cell suspension.

The cell suspension was put to a flask, and 2.5 ml of a 10% glucose solution and trichloroethylene (final concentration: 1 mM) were added thereto. The flask was sealed and incubated with shaking at 30° C. for 12 hours to let the cells act on the trichloroethylene. An aliquot of the culture was subjected to gas chromatography to measure the intensity ($I_1$) of the signal assigned to trichloroethylene remaining in the culture.

For comparison, 50 ml of a cell-free medium ($K_2HPO_4$ 1.74 g, $MgSO_4 \cdot 7H_2O$ 1.5 g, $FeSO_4 \cdot H_2O$ 0.05 g, deionized water 1 l; adjusted to pH 8.0) was put to a flask of the same volume as used above, and 2.5 ml of a 10% glucose solution and trichloroethylene (final concentration: 1 mM) were added thereto. The flask was sealed and incubated with shaking at 30° C. for 12 hours. An aliquot of the culture was subjected to gas chromatography to measure the intensity ($I_2$) of the signal assigned to trichloroethylene remaining in the culture. The signal intensity ($I_2$) was 95% or more of the initial signal intensity ($I_0$) measured on the medium immediately after addition of trichloroethylene.

Signal intensity ($I_1$) was about 2% of signal intensity ($I_2$), indicating that the trichloroethylene concentration in the medium was reduced to about 2% and about 98% of trichloroethylene had been degraded with the growth of the microorganism. In the above treatment, it is understood that trichloroethylene is converted first into trichloroethylene oxide.

It was found that cells of *Nocardia corallina* B-276 (FERM P-4094; FERM BP-5124; ATCC 31338) grown with glucose as the carbon source are capable of degrading efficiently trichloroethylene, confirming also that the alkene monooxygenase is maintained as an effective enzyme in the cells grown with glucose as the carbon source.

EXAMPLE 2

LB medium (1.5 ml) (a liquid medium containing 10 g of Bacto-trypton, 5 g of Bacto-yeast extract, 10 g of sodium chloride, and deionized water to make 1 l, adjusted to pH 7.2 with a 1N aqueous sodium chloride solution, steam sterilized by autoclaving at 120° C. for 15 minutes) containing 50 µg/ml of ampicillin was inoculated with one loopful of *E. coli* JM109 (pDBB-1) (FERM BP-4250) using a platinum loop, which is a transformant having an alkene monooxygenase gene of *Nocardia corallina* B-276 origin, and incubated at 37° C. overnight (about 14 hours) for previous proliferation of the microorganism. Then, 100 ml of LB medium containing 50 µg/ml of ampicillin was inoculated with the resulting culture and incubated at 37° C. for 2 hours. To the culture was added isopropyl-β-D-thiogalactopyranoside (IPTG) at a final concentration of 1 mM, followed by further shake culture at 37° C. for 5 hours. A 10 ml aliquot of the resulting culture was centrifuged to collect the microbial cells, which were suspended in 2 ml of a minimal medium ($K_2HPO_4$ 1.74 g, $MgSO_4 \cdot 7H_2O$ 1.5 g, $FeSO_4 \cdot H_2O$ 0.05 g, deionized water 1 l; adjusted to pH 8.0) to prepare a cell suspension.

To the cell suspension in a flask were added 100 µl of a 10% glucose solution and trichloroethylene (final concentration: 1 mM), and the flask was sealed and shake-cultured at 30° C. for 12 hours to allow the cells to act on the trichloroethylene. An aliquot of the culture was subjected to gas chromatography to measure the intensity ($I_4$) of the signal assigned to trichloroethylene remaining in the culture.

For comparison, 2 ml of a cell-free medium ($K_2HPO_4$ 1.74 g, $MgSO_4 \cdot 7H_2O$ 1.5 g, $FeSO_4 \cdot H_2O$ 0.05 g, deionized water 1 l; adjusted to pH 8.0) was put to a flask of the same volume as used above, and 100 µl of a 10% glucose solution and trichloroethylene (final concentration: 1 mM) were added thereto. The flask was sealed and shake-cultured at 30° C. for 12 hours. An aliquot of the culture was subjected to gas chromatography to measure the intensity ($I_5$) of the signal assigned to trichloroethylene remaining in the culture. Signal intensity ($I_5$) was 95% or more of the initial signal intensity ($I_3$).

Signal intensity ($I_4$) was about 83% of signal intensity ($I_3$), indicating that the trichloroethylene concentration in the medium was reduced to about 83%, and about 17% of trichloroethylene had been degraded with the growth of the microorganism. In the above treatment, it is understood that trichloroethylene is converted first into trichloroethylene oxide.

It was found that cells of *E. coli* JM109 (pDBB-1) (FERM BP-4250) cultivated with glucose as the carbon source are capable of degrading efficiently trichloroethylene, confirming also that the alkene monooxygenase is maintained as an effective enzyme in the cells cultivated with glucose as the carbon source.

EXAMPLE 3

In the biological oxidation of trichloroethylene with *Nocardia corallina* B-276 (FERM P-4095; FERM BP-5124; ATCC 31338), the influence of the trichloroethylene concentration on the reaction rate was examined as follows.

*Nocardia corallina* B-276 (FERM P-4094; FERM BP-5124; ATCC 31338) was previously proliferated in the same manner as described in Example 1. The microbial cells collected were suspended in a medium ($K_2HPO_4$ 1.74 g, $MgSO_4 \cdot 7H_2O$ 1.5 g, $FeSO_4 \cdot H_2O$ 0.05 g, deionized water 1 l; adjusted to pH 8.0) to prepare a cell suspension.

In a 17 ml-volume flask was put 2 ml of the cell suspension, 100 µl of a 10% glucose solution added as an energy source, a varied amount of trichloroethylene added thereto, and the flask sealed and incubated at 35° C. for 5 hours while shaking to allow the cells to act on the trichloroethylene. The cell concentration was 2.44 g/l. A 1 ml aliquot of the gas was taken out every 1 hour from the gas phase of the sealed flask and analyzed by gas chromatography (column: Porapak Q) to measure the gaseous trichloroethylene concentration. The trichloroethylene concentration remaining in the liquid phase was calculated from the gaseous phase trichloroethylene concentration. This calculation was made on the assumption that the partitioning of trichloroethylene between the gas and liquid phases in the vial are obeyed by the partition law.

Figure 2:
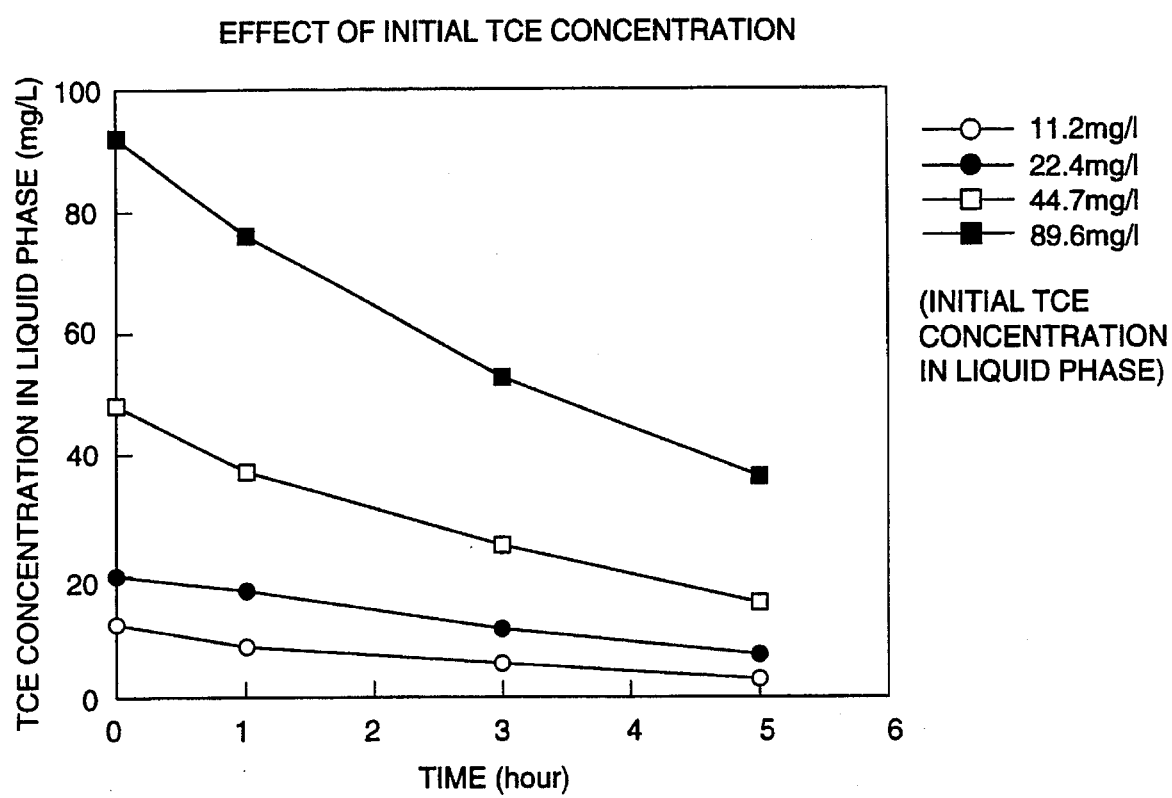
FIG. 2 is a plot of change in trichloroethylene concentration remaining in the liquid phase against time in the reaction system using *Nocardia corallina* B-276 (FERM P-4094; FERM BP-5124; ATCC 31338) and containing trichloroethylene at varying initial concentrations.
Figure 3:
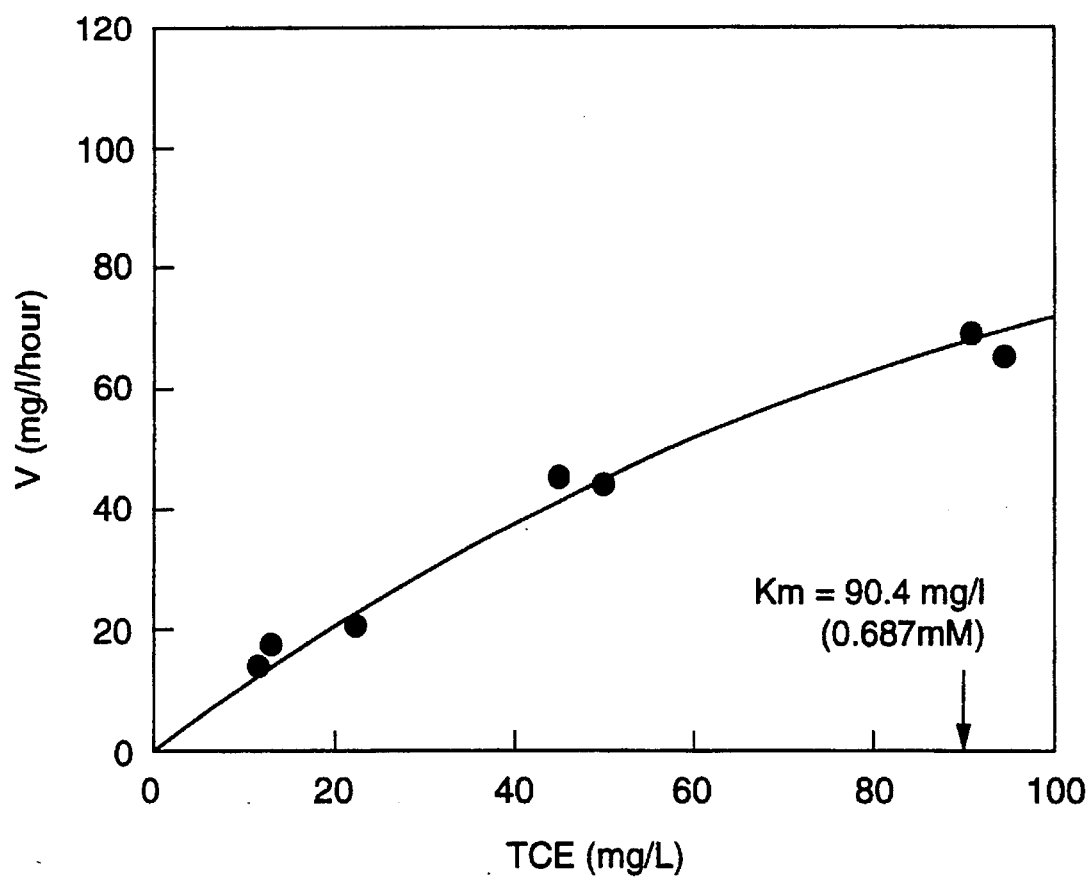
FIG. 3 is a graph showing the dependence of reaction rate upon initial trichloroethylene concentration in the reaction system using *Nocardia corallina* B-276 (FERM P-4094; FERM BP-5124; ATCC 31338).

FIG. 2 shows the change in trichloroethylene (TCE) concentration in the liquid phase with time, with the amount of trichloroethylene added (initial trichloroethylene concentration in the liquid phase) being varied. FIG. 3 is a graph of rate of reduction of liquid phase trichloroethylene concentration plotted against initial trichloroethylene concentration. As can be seen from these results, the reaction rate of *Nocardia corallina* B-276 (FERM P-4094; FERM BP-5124; ATCC 31338) is almost proportional to the initial trichloroethylene concentration in the liquid phase, and no obvious inhibition is observed at least up to 90 mg/l of the initial trichloroethylene concentration. The Michaelis constant Km of the trichloroethylene substrate in this enzyme reaction was 90.4 mg/l (0.678 mM) as calculated based on the results of FIG. 3.

Thus, *Nocardia corallina* B-276 (FERM P-4094; FERM BP-5124; ATCC 31338) does not undergo inhibition, even at a high trichloroethylene concentration, and maintains high efficiency in degradation of TCE in the presence of excessive TCE.

Further, the influence of temperature on the rate of biological degradation of trichloroethylene with *Nocardia corallina* B-276 (FERM P-4094; FERM BP-5124; ATCC 31338) was examined in the same manner as described above, except that the cell concentration was set at 8.0 g/l, the initial trichloroethylene concentration in the liquid phase was fixed at 50.1 mg/l and the temperature of the medium was varied. At the time point of 60 minutes from the commencement of the treatment, the trichloroethylene concentration in the liquid phase was measured, and its ratio to the initial trichloroethylene concentration was taken as a measure of reaction rate. FIG. 4 shows, as an example, reaction rate was plotted against medium temperature. It is seen that the reaction rate reaches the maximum at around 35° C. It has thus been ascertained that the treatment is preferably conducted from 30° to 45° C., especially at 35°±5° C.

EXAMPLE 4

To demonstrate that Nocardia corallina B-276 (FERM P-4094; FERM BP-5124; ATCC 31338) is capable of degrading not only trichloroethylene but other chlorine-substituted ethylenes, experiments were conducted on 1,1-dichloroethylene (1,1-DCE), cis-1,2-dichloroethylene (CIS-DCE) and trans-1,2-dichloroethylene (TRANS-DCE) under the following conditions. Experiments were also carried on tetrachloroethylene (perchloroethylene) (PCE) and 1,2-dichloroethane (1,2-DCA).

Figure 5A:
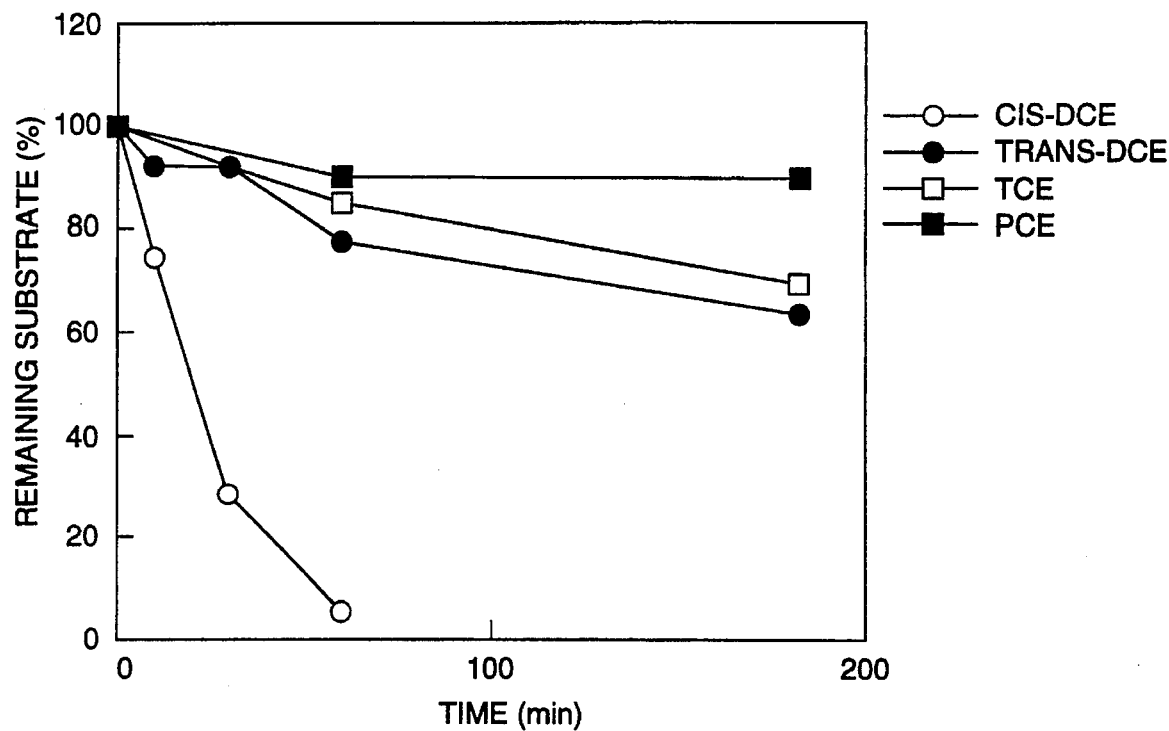
FIG. 5A is a plot of change in concentration of cis-1,2-dichloroethylene (CIS-DCE), trans-1,2-dichloroethylene (TRANS-DCE), trichloroethylene (TCE), or perchloroethylene (PCE) against time in the reaction system using *Nocardia corallina* B-276 (FERM P-4094; FERM BP-5124; ATCC 31338).
Figure 5B:
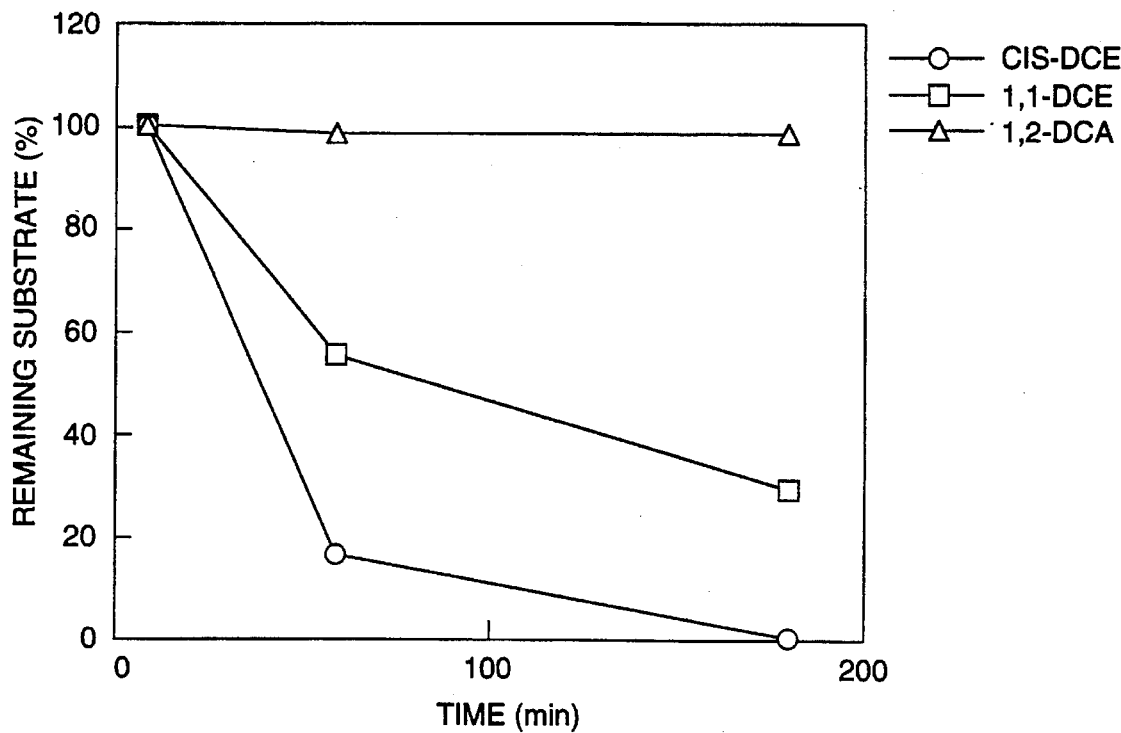
FIG. 5B is a plot of change in concentration of cis-1,2-dichloroethylene (CIS-DCE), 1,1-dichloroethylene (1,1-DCE), or 1,2-dichloroethane (1,2-DCA) against time in the reaction system using *Nocardia corallina* B-276 (FERM P-4094; FERM BP-5124; ATCC 31338).

The initial concentration of each substrate in the liquid phase was selected so as not to exceed 20 mg/l, i.e., the range in which no inhibition on the enzyme reaction is expected. Specifically, the substrate was added in an amount of 100 mg which corresponded to 11.2 mg/l of trichloroethylene in terms of initial concentration in the liquid phase. Previous proliferation and preparation of cell suspension were made in a similar manner to Example 1. The cell concentration during the reaction was set at 4.0 g/l or 8.0 g/l, and the concentration of the substrate remaining in the gas phase was measured with time in the same manner as in Example 3 and converted to the concentration in the liquid phase, from which the reaction rate was calculated. FIG. 5A and also FIG. 5B show, as an example, the change in remaining substrate concentration in the liquid phase was plotted against time.

The reaction rate for each substrate and cell concentration used in each reaction are shown in Table 1 below.

TABLE 1

| Substrate | Reaction Rate (mg/l/hr) | Cell Concentration (g/l) |
| --- | --- | --- |
| cis-1,2-Dichloroethylene | 72.2 | 4.0 |
| 1,1-Dichloroethylene | 14.8 | 8.0 |
| trans-1,2-dichloroethylene | 6.5 | 4.0 |
| Trichloroethylene | 5.5 | 4.0 |
| Tetrachloroethylene | 0 | 4.0 |
| 1,2-Dichloroethane | 0 | 4.0 |

It was confirmed that chlorine-substituted ethylenes other than trichloroethylene, i.e., 1,1-dichloroethylene, cis-1,2-dichloroethylene, and trans-1,2-dichloroethylene can be degraded as well by utilizing Nocardia corallina B-276 (FERM P-4094; FERM BP-5124; ATCC 31338).

It is seen, on the contrary, that tetrachloroethylene (perchloroethylene) and 1,2-dichloroethane cannot be degraded. Since 1,2-dichloroethane has no carbon-carbon double bond, it could not be converted into an epoxide by the action of an alkene monooxygenase.

It is revealed from this result that the enzyme reaction involves conversion to an epoxide by the action of an alkene monooxygenase in the initial stage reaction. Further considering that no enzyme reaction takes place on tetrachloroethylene (perchloroethylene) while the enzyme reaction shows the highest efficiency on cis-1,2-dichloroethylene, it is understood that the hydrogen atom remaining on the carbon-carbon double bond is indispensable for the binding process of the substrate to the enzyme. This is also reflected in the fact that the reaction rate on cis-1,2-dichloroethylene is markedly high and decreases little by little in the order of 1,1-dichloroethylene (corresponding to 7.4 mg/l hr), trans-1,2-dichloroethylene (6.5 mg/l hr), and trichloroethylene (5.5 mg/l hr). It is considered that there is no significant difference in reaction rate among 1,1-dichloroethylene, trans-1,2-dichloroethylene, and trichloroethylene. Furthermore, it is believed the enzyme reaction takes place rapidly on vinyl chloride (chloroethylene) having two hydrogen atoms remaining on the cis position similarly to cis-1,2-dichloroethylene. The reaction rate on vinyl chloride (chloroethylene) was not verified because this compound is a carcinogen and is gaseous at ambient temperature and therefore meets difficulty in measurement by the above-described test method.

It was found that cells of Nocardia corallina B-276 (FERM P-4094; FERM BP-5124; ATCC 31338) grown with glucose as the carbon source are capable of degrading efficiently chlorine-substituted ethylenes, i.e., cis-1,2-dichloroethylene, 1,1-dichloroethylene, trans-1,2-dichloroethylene, trichloroethylene, and much probably and vinyl chloride (chloroethylene), confirming also that the alkene monooxygenase is maintained as an effective enzyme in the cells grown with glucose as the carbon source.

It has been confirmed from all the above results that the treating method according to the present invention utilizes the process in which a chlorine-substituted ethylene is converted into a corresponding epoxide through alkene monooxygenase reaction and that not only Nocardia corallina B-276 (FERM P-4094; FERM BP-5124; ATCC 31338) but any other microorganisms capable of producing an alkene monooxygenase of the same type as produced from the above specific strain may be utilized. In addition, any microorganism that can degrade trichloroethylene would degrade 1,1-dichloroethylene, cis-1,2-dichloroethylene, trans-1,2-dichloroethylene, and vinyl chloride (chloroethylene) as well.

According to the method of the present invention, a chlorine-substituted ethylene having 1 to 3 chlorine atoms can be biologically oxidized and degraded at high efficiency by culturing an alkene-assimilating microorganism or a microorganism capable of producing an alkene monooxygenase which catalyzes oxidation of an alkene to a corresponding epoxide, in a medium containing the chlorine-substituted ethylene to be treated. The method of the present invention may be used as the most suited method for the degradative treatment of a chlorine-substituted ethylene dispersed in a large quantity of a medium in an extremely low concentration, such as chlorine-substituted ethylenes having 1 to 3 carbon atoms, such as trichloroethylene, present in contaminated water or exhaust gas in very low concentrations.

While the invention has been described in detail and with reference to specific examples thereof, it will be apparent to one skilled in the art that various changes and modifications can be made therein without departing from the spirit and scope thereof.

What is claimed is:

1. A DNA fragment containing a gene encoding an alkene monooxygenase obtained from *Nocardia corallina* B-276 (FERM P-4094; FERM BP-5124; ATCC 31338) as depicted in Seq. ID No:1.

2. A transformant microorganism carrying an expression vector containing the DNA fragment of claim 1, wherein the host microorganism is *E. coli* JM109.

3. The transformant microorganism according to claim 2, which is *E. coli* JM109 (pDBB-1) (FERM BP-4250).

4. A method for biologically degradative-treating a chlorine-substituted ethylene comprising culturing a microorganism capable of producing an alkene monooxygenase which produces said alkene monooxygenase when said microorganism is grown using carbohydrates as a sole carbon source, in a medium containing a chlorine-substituted ethylene having 1 to 3 chlorine atoms whereby said chlorine-substituted ethylene is oxidized to a corresponding epoxide by said microorganism, wherein said microorganism is precultured using carbohydrates as a sole carbon source.

5. A method for biologically degradative-treating a chlorine-substituted ethylene comprising culturing a microorganism capable of growing in a medium containing an alkene as a sole carbon source, which produces an oxygenase participating in said alkene metabolism when said microorganism is grown using carbohydrates as a sole carbon source in a medium containing a chlorine-substituted ethylene having 1 to 3 chlorine atoms whereby said chlorine-substituted ethylene is oxidized to a corresponding epoxide by said microorganism, wherein said microorganism is precultured using carbohydrates as a sole carbon source.

6. A method for biologically degradative-treating a chlorine-substituted ethylene comprising culturing a transformant microorganism that produces an alkene monooxygenase, which has is a plasmid vector containing a gene encoding an alkene monooxygenase, wherein said gene is obtained from *Nocardia corallina* B-276 (FERM P-4094; FERM BP-5124; ATCC 31338) in a medium containing a chlorine-substituted ethylene having 1 to 3 chlorine atoms whereby said chlorine-substituted ethylene is oxidized to a corresponding epoxide by said microorganism, wherein said microorganism is precultured using carbohydrates as a sole carbon source.

7. A method for biologically degradative-treating a chlorine-substituted ethylene according to claim 4, 5, or 6, wherein said microorganism belongs to a genus selected from the group consisting of Nocardia, Rhodococcus, Xanthobacter, and Mycobacterium.

8. A method for biologically degradative-treating a chlorine-substituted ethylene according to claim 6, wherein said transformant is *Escherichia coli*.

9. A method for biologically degradative-treating a chlorine-substituted ethylene comprising culturing *Nocardia corallina* B-276 (FERM P-4094; FERM BP-5124; ATCC 31338) in a medium containing a chlorine-substituted ethylene having 1 to 3 chlorine atoms, wherein said chlorine-substituted ethylene is oxidized to a corresponding epoxide by said microorganism.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 6379 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( B ) STRAIN: Nocardia corallina B-276 (FERM P-4094; FERM
        BP-5124; ATCC 31338)

( i x ) FEATURE:
        ( A ) NAME/KEY: CDS
        ( B ) LOCATION: 910..1935
        ( D ) OTHER INFORMATION: /product="amoA"

( i x ) FEATURE:
        ( A ) NAME/KEY: CDS
        ( B ) LOCATION: 1935..2285
        ( D ) OTHER INFORMATION: /product="amoB"

( i x ) FEATURE:
        ( A ) NAME/KEY: CDS
        ( B ) LOCATION: 2300..3802
        ( D ) OTHER INFORMATION: /product="amoC"

( i x ) FEATURE:
        ( A ) NAME/KEY: CDS
        ( B ) LOCATION: 3805..4830
        ( D ) OTHER INFORMATION: /product="amoD"

( x i ) SEQUENCE DESCRIPTION: SEQ ID NO:1:

```
GGATCCCCAG GTCCCGAGCC ACCGCGGCGA TCGACTTCCC CGTCTCATGC ACGATCCGCA      60

CAGCCCCCTC ACGGAACTCC CGGTCGTACT TTTCCGCTTC TCTGACATCC CTACCCCTTA     120

TAGCTGATGC CTCCACGGTC TCGGGGAATG CCAATATGAC TTGGTCAGAT CGTAGGCGGC     180

AAGAACCATG GCTTCCTTGG CGGACTTCAC AGGGGCCTCT CCTCGAGGGC TCGTTCGGGC     240

ATGGGTAGCA CCGTCGAGCG AACCCGAGGA GAGGCCCCGA TCCGGGGAGG CGATCGGGAT     300

GAACGGGGAC GTGTCGAGAA TCGATCAGAC TTGGTGGGCA GATTCGTGTC CGCCGGTGGG     360

CAGAACCCGA TGGCCATCCA CGGGCACTTT CGTGGCCATC AGTGGGCGGT TTCGTGACCC     420

CCTATGGGCA GTTTTCCATG GCCGCCGACA CACAGGCCCG CACCGATGAC GAGGTACTGC     480

ACGACCCGGC CGACCGCGCG GTGGTTTGCT GCAACAAATG ACAACTTGAT CAACGCATCG     540

ATCACGACCG GCGCCACTAA CGCCGCCGCG GCAAGCATCG ACATCAACAC CATCGCGACC     600

GTCCGCCCTT CACATCGACG ACACCTCGGT CGATGTGTGC ATACCGCATG CATCCGGCAA     660

GAACCCCGCG GACTCCGCAG CCGGTGCGGC TAGCCGATTT CACCCAACCT GGGACGTTGG     720

CTACGGAACG TCTCGTGGAT GACGGCGCCT GCATGCTGCA TAGACCCGTC CGTGGCCGCA     780

ATGTCCTGGT GAGGCATGCG AGCGGCTTCG ATTCCTCTCG GCGGGGCCAA GACCGGCGGG     840

CCGCGCCTGT CTAACATCGC GGCACAAGGA AATCGCAACC GGACCGAAAC GATGGAAGGC     900
```

| GTAGCGATG | ACG | ACA | GAG | GCG | ACG | GTG | GCC | CGA | CCG | GTG | GAG | CTC | GAA | 948 |
|---|---|---|---|---|---|---|---|---|---|---|---|---|---|---|
| | Thr | Thr | Glu | Ala | Thr | Val | Ala | Arg | Pro | Val | Glu | Leu | Glu | |
| | 1 | | | 5 | | | | | 10 | | | | | |

| | | | | | | | | | | | | | | | | |
|---|---|---|---|---|---|---|---|---|---|---|---|---|---|---|---|---|
| GGT | CAC | CGG | ACA | TTC | ACC | TGG | TTC | ACG | CCC | GCC | AGG | CGA | AAG | CCG | ACG | 996 |
| Gly | His | Arg | Thr | Phe | Thr | Trp | Phe | Thr | Pro | Ala | Arg | Arg | Lys | Pro | Thr | |
| | 15 | | | | | 20 | | | | | 25 | | | | | |
| GAG | TAC | GAG | CTC | TAC | ACC | GTG | GGT | CAA | CAG | TCC | ACT | CCG | GAC | GAG | TGG | 1044 |
| Glu | Tyr | Glu | Leu | Tyr | Thr | Val | Gly | Gln | Gln | Ser | Thr | Pro | Asp | Glu | Trp | |
| 30 | | | | | 35 | | | | | 40 | | | | | 45 | |
| CTG | CAT | GTG | GAC | TGG | CCG | CTG | CGC | TTC | GAC | GAC | GGC | CGC | GCC | CCG | TGG | 1092 |
| Leu | His | Val | Asp | Trp | Pro | Leu | Arg | Phe | Asp | Asp | Gly | Arg | Ala | Pro | Trp | |
| | | | | 50 | | | | | 55 | | | | | 60 | | |
| GAG | GAG | GAG | TCG | AGT | GCG | GTA | CGG | ACC | TCG | GAG | TGG | TCG | GCT | TAC | CGC | 1140 |
| Glu | Glu | Glu | Ser | Ser | Ala | Val | Arg | Thr | Ser | Glu | Trp | Ser | Ala | Tyr | Arg | |
| | | | 65 | | | | | 70 | | | | | 75 | | | |
| GAC | CCA | CAC | CAA | CTG | TGG | CAG | CGT | CCC | TAC | GTC | AGC | ACG | TGC | AAC | CAG | 1188 |
| Asp | Pro | His | Gln | Leu | Trp | Gln | Arg | Pro | Tyr | Val | Ser | Thr | Cys | Asn | Gln | |
| | | 80 | | | | | 85 | | | | | 90 | | | | |
| GAC | CAG | CAG | GCC | CTC | GCG | CGG | CTG | GTC | CCC | GTC | CTG | ACC | ATG | GGG | TCG | 1236 |
| Asp | Gln | Gln | Ala | Leu | Ala | Arg | Leu | Val | Pro | Val | Leu | Thr | Met | Gly | Ser | |
| | 95 | | | | | 100 | | | | | 105 | | | | | |
| GCG | GCG | ATC | ACG | CCC | ATC | TGG | TCG | CAG | AAG | ATC | CTC | GCC | AGG | TCC | TAC | 1284 |
| Ala | Ala | Ile | Thr | Pro | Ile | Trp | Ser | Gln | Lys | Ile | Leu | Ala | Arg | Ser | Tyr | |
| 110 | | | | | 115 | | | | | 120 | | | | | 125 | |
| GCC | GCC | TGG | CCA | TTC | GTC | GAG | TAC | GGG | CTC | TTC | CTG | AGC | CTG | GCC | TAC | 1332 |
| Ala | Ala | Trp | Pro | Phe | Val | Glu | Tyr | Gly | Leu | Phe | Leu | Ser | Leu | Ala | Tyr | |
| | | | | 130 | | | | | 135 | | | | | 140 | | |
| GCC | GTG | CGC | CAG | GCC | ATG | TCC | GAC | ACG | GTC | CAG | TTC | AGC | GTG | GTG | TTC | 1380 |
| Ala | Val | Arg | Gln | Ala | Met | Ser | Asp | Thr | Val | Gln | Phe | Ser | Val | Val | Phe | |
| | | | 145 | | | | | 150 | | | | | 155 | | | |
| CAG | GCC | GTG | GAC | CGC | ATG | CGG | CTG | CTC | CAG | GAC | ATC | GTC | CAC | CAC | CTG | 1428 |
| Gln | Ala | Val | Asp | Arg | Met | Arg | Leu | Leu | Gln | Asp | Ile | Val | His | His | Leu | |
| | | 160 | | | | | 165 | | | | | 170 | | | | |
| GAC | CAC | CTG | CAG | GAG | TCG | CCG | GAA | TTC | AGC | GAC | GCC | GGG | GCC | CGC | GAG | 1476 |
| Asp | His | Leu | Gln | Glu | Ser | Pro | Glu | Phe | Ser | Asp | Ala | Gly | Ala | Arg | Glu | |
| | 175 | | | | | 180 | | | | | 185 | | | | | |
| GCC | TGG | ATG | TCC | GAC | TCC | ACC | CTG | GTC | CCG | ATC | CGG | GAA | GTG | ATC | GAG | 1524 |
| Ala | Trp | Met | Ser | Asp | Ser | Thr | Leu | Val | Pro | Ile | Arg | Glu | Val | Ile | Glu | |
| 190 | | | | | 195 | | | | | 200 | | | | | 205 | |
| CGC | ATC | GCC | GCC | AGC | CAG | GAC | TGG | GTG | GAG | ATC | CTG | GTC | GCC | GGC | ACG | 1572 |
| Arg | Ile | Ala | Ala | Ser | Gln | Asp | Trp | Val | Glu | Ile | Leu | Val | Ala | Gly | Thr | |
| | | | | 210 | | | | | 215 | | | | | 220 | | |
| CTC | GTC | TTC | GAG | CCT | CTG | GTC | GGC | CAC | CTG | GCG | AAG | GCC | GAG | TTG | TTC | 1620 |
| Leu | Val | Phe | Glu | Pro | Leu | Val | Gly | His | Leu | Ala | Lys | Ala | Glu | Leu | Phe | |
| | | | 225 | | | | | 230 | | | | | 235 | | | |
| AGC | CGC | CGT | GCG | CCA | ATG | TTC | GGG | GAC | GGG | ACC | CCG | CCG | GCG | GTG | CTG | 1668 |
| Ser | Arg | Arg | Ala | Pro | Met | Phe | Gly | Asp | Gly | Thr | Pro | Pro | Ala | Val | Leu | |
| | | 240 | | | | | 245 | | | | | 250 | | | | |
| GCG | TCG | GCC | CTG | CTG | GAC | AGC | GGC | AGG | CAC | CTC | GAA | TCG | GTC | CAG | GCG | 1716 |
| Ala | Ser | Ala | Leu | Leu | Asp | Ser | Gly | Arg | His | Leu | Glu | Ser | Val | Gln | Ala | |
| | 255 | | | | | 260 | | | | | 265 | | | | | |
| CTC | GTC | CGC | CTC | GTC | TGC | CAA | GAC | CCC | GTC | CAT | GGC | GAC | CAG | AAC | CAG | 1764 |
| Leu | Val | Arg | Leu | Val | Cys | Gln | Asp | Pro | Val | His | Gly | Asp | Gln | Asn | Gln | |
| 270 | | | | | 275 | | | | | 280 | | | | | 285 | |
| GCG | ACT | GTG | CGG | CGG | TGG | ATC | GAG | GAA | TGG | CAG | CCG | CGG | TGC | AAG | GCG | 1812 |
| Ala | Thr | Val | Arg | Arg | Trp | Ile | Glu | Glu | Trp | Gln | Pro | Arg | Cys | Lys | Ala | |
| | | | | 290 | | | | | 295 | | | | | 300 | | |
| GCG | GCC | CAG | TCC | TTC | CTG | CCG | ACG | TTC | TCC | GAC | TGC | GGC | ATC | GAC | GCC | 1860 |
| Ala | Ala | Gln | Ser | Phe | Leu | Pro | Thr | Phe | Ser | Asp | Cys | Gly | Ile | Asp | Ala | |
| | | | 305 | | | | | 310 | | | | | 315 | | | |
| AAG | GAA | AGC | GCC | AAC | GCG | CTG | TCC | CGG | GCG | CTG | GCG | AAC | CAG | CGG | GCC | 1908 |
| Lys | Glu | Ser | Ala | Asn | Ala | Leu | Ser | Arg | Ala | Leu | Ala | Asn | Gln | Arg | Ala | |
| | | 320 | | | | | 325 | | | | | 330 | | | | |

| | | | | | | | | | | | | | | | | |
|---|---|---|---|---|---|---|---|---|---|---|---|---|---|---|---|---|
| GCC | GTC | GAG | GGC | GCC | GGC | ATC | ACG | GCATG | ACA | GAC | GTT | AAG | GAG | ACC | | 1955 |
| Ala | Val | Glu | Gly | Ala | Gly | Ile | Thr | Ala | | | | | | | | |
| | 335 | | | | | 340 | | | | | | | | | | |
| | | | | | | | | Met | Thr | Asp | Val | Lys | Glu | Thr | | |
| | | | | | | | | 1 | | | | 5 | | | | |
| ACT | GTG | ACC | AGC | ACC | CCC | TCG | GCC | GCC | GTG | CCG | GGA | ACC | AAG | AAC | CGC | 2003 |
| Thr | Val | Thr | Ser | Thr | Pro | Ser | Ala | Ala | Val | Pro | Gly | Thr | Lys | Asn | Arg | |
| | | 10 | | | | 15 | | | | | 20 | | | | | |
| CGC | GTT | GGT | ATC | TCG | CTG | ATC | AGC | AGC | AGC | GAC | ACC | GAG | GCA | GCT | GTC | 2051 |
| Arg | Val | Gly | Ile | Ser | Leu | Ile | Ser | Ser | Ser | Asp | Thr | Glu | Ala | Ala | Val | |
| | 25 | | | | | 30 | | | | | 35 | | | | | |
| GAG | CAC | ATC | GCG | GAG | ACC | CAG | CCG | GAC | GCG | AAG | ATC | GAC | TTT | CGG | GAC | 2099 |
| Glu | His | Ile | Ala | Glu | Thr | Gln | Pro | Asp | Ala | Lys | Ile | Asp | Phe | Arg | Asp | |
| 40 | | | | | 45 | | | | | 50 | | | | | 55 | |
| TGC | TTC | TAC | AAG | ATC | GAG | CGT | GAC | GGG | CAG | CTC | AGT | TTC | GAC | ATG | GCA | 2147 |
| Cys | Phe | Tyr | Lys | Ile | Glu | Arg | Asp | Gly | Gln | Leu | Ser | Phe | Asp | Met | Ala | |
| | | | | 60 | | | | | 65 | | | | | 70 | | |
| GAG | CTC | AGT | GAG | ATC | GCC | GGT | CGC | GAC | ATC | GAC | ACC | GAC | ATC | TTC | CTG | 2195 |
| Glu | Leu | Ser | Glu | Ile | Ala | Gly | Arg | Asp | Ile | Asp | Thr | Asp | Ile | Phe | Leu | |
| | | | 75 | | | | | 80 | | | | | 85 | | | |
| GTG | AAC | ATG | AGC | ACC | TAC | TAC | GGC | CGG | ATC | GTC | GTC | AGT | GAC | GGC | CGG | 2243 |
| Val | Asn | Met | Ser | Thr | Tyr | Tyr | Gly | Arg | Ile | Val | Val | Ser | Asp | Gly | Arg | |
| | | 90 | | | | | 95 | | | | | 100 | | | | |
| GTC | GAC | ATC | TAC | GCC | GAA | ATC | CAG | CCG | GCC | CGC | TTC | AAG | GAC | | | 2285 |
| Val | Asp | Ile | Tyr | Ala | Glu | Ile | Gln | Pro | Ala | Arg | Phe | Lys | Asp | | | |
| 105 | | | | | 110 | | | | | 115 | | | | | | |
| TGAGAGGAAA | CACC | ATG | GCA | TCG | AAC | CCC | ACC | CAG | CTC | CAC | GAG | AAG | TCG | | | 2335 |
| | | Met | Ala | Ser | Asn | Pro | Thr | Gln | Leu | His | Glu | Lys | Ser | | | |
| | | 1 | | | | 5 | | | | | 10 | | | | | |
| AAG | TCC | TAC | GAC | TGG | GAC | TTC | ACC | TCC | GTC | GAG | CGG | CGC | CCC | AAG | TTC | 2383 |
| Lys | Ser | Tyr | Asp | Trp | Asp | Phe | Thr | Ser | Val | Glu | Arg | Arg | Pro | Lys | Phe | |
| | | 15 | | | | 20 | | | | | 25 | | | | | |
| GAG | ACG | AAG | TAC | AAG | ATG | CCC | AAG | AAG | GGC | AAG | GAC | CCG | TTC | CGC | GTC | 2431 |
| Glu | Thr | Lys | Tyr | Lys | Met | Pro | Lys | Lys | Gly | Lys | Asp | Pro | Phe | Arg | Val | |
| | 30 | | | | 35 | | | | | 40 | | | | | | |
| CTG | ATC | CGT | GAC | TAC | ATG | AAG | ATG | GAA | GCG | GAG | AAG | GAC | GAC | CGG | ACC | 2479 |
| Leu | Ile | Arg | Asp | Tyr | Met | Lys | Met | Glu | Ala | Glu | Lys | Asp | Asp | Arg | Thr | |
| 45 | | | | | 50 | | | | | 55 | | | | | 60 | |
| CAT | GGC | TTC | CTC | GAC | GGC | GCC | GTG | CGG | ACG | CGT | GAG | GCC | ACC | AGG | ATT | 2527 |
| His | Gly | Phe | Leu | Asp | Gly | Ala | Val | Arg | Thr | Arg | Glu | Ala | Thr | Arg | Ile | |
| | | | | 65 | | | | | 70 | | | | | 75 | | |
| GAG | CCG | CGG | TTC | GCT | GAG | GCC | ATG | AAG | ATC | ATG | GTG | CCG | CAG | CTG | ACC | 2575 |
| Glu | Pro | Arg | Phe | Ala | Glu | Ala | Met | Lys | Ile | Met | Val | Pro | Gln | Leu | Thr | |
| | | | 80 | | | | | 85 | | | | | 90 | | | |
| AAC | GCC | GAG | TAC | CAG | GCG | GTG | GCG | GGC | TGC | GGA | ATG | ATC | ATC | TCG | GCC | 2623 |
| Asn | Ala | Glu | Tyr | Gln | Ala | Val | Ala | Gly | Cys | Gly | Met | Ile | Ile | Ser | Ala | |
| | | 95 | | | | | 100 | | | | | 105 | | | | |
| GTC | GAG | AAC | CAG | GAG | CTC | CGT | CAG | GGC | TAC | GCC | GCT | CAG | ATG | CTC | GAT | 2671 |
| Val | Glu | Asn | Gln | Glu | Leu | Arg | Gln | Gly | Tyr | Ala | Ala | Gln | Met | Leu | Asp | |
| 110 | | | | | 115 | | | | | 120 | | | | | | |
| GAG | GTG | CGG | CAC | GCG | CAG | CTC | GAG | ATG | ACG | CTA | CGC | AAC | TAC | TAC | GCG | 2719 |
| Glu | Val | Arg | His | Ala | Gln | Leu | Glu | Met | Thr | Leu | Arg | Asn | Tyr | Tyr | Ala | |
| 125 | | | | | 130 | | | | | 135 | | | | | 140 | |
| AAG | CAC | TGG | TGC | GAT | CCC | TCC | GGC | TTC | GAC | ATC | GGT | CAG | CGC | GGC | CTG | 2767 |
| Lys | His | Trp | Cys | Asp | Pro | Ser | Gly | Phe | Asp | Ile | Gly | Gln | Arg | Gly | Leu | |
| | | | | 145 | | | | | 150 | | | | | 155 | | |
| TAC | CAG | CAC | CCC | GCG | GGG | CTG | GTG | TCC | ATC | GGC | GAG | TTC | CAG | CAC | TTC | 2815 |
| Tyr | Gln | His | Pro | Ala | Gly | Leu | Val | Ser | Ile | Gly | Glu | Phe | Gln | His | Phe | |
| | | | 160 | | | | | 165 | | | | | 170 | | | |
| AAT | ACT | GGT | GAC | CCG | CTT | GAC | GTC | ATC | ATC | GAT | CTC | AAC | ATC | GTG | GCC | 2863 |

|     |     |     |     |     |     |     |     |     |     |     |     |     |     |     |     |
|-----|-----|-----|-----|-----|-----|-----|-----|-----|-----|-----|-----|-----|-----|-----|-----|
| Asn | Thr | Gly | Asp | Pro | Leu | Asp | Val | Ile | Ile | Asp | Leu | Asn | Ile | Val | Ala |
|     |     | 175 |     |     |     |     | 180 |     |     |     |     | 185 |     |     |     |

```
GAG  ACG  GCG  TTC  ACG  AAC  ATC  CTG  CTG  GTG  GCC  ACT  CCA  CAG  GTC  GCC      2911
Glu  Thr  Ala  Phe  Thr  Asn  Ile  Leu  Leu  Val  Ala  Thr  Pro  Gln  Val  Ala
          190                 195                 200

GTG  GCC  AAC  GGG  GAC  AAC  GCG  ATG  GCC  AGC  GTG  TTC  CTC  TCG  ATC  CAG      2959
Val  Ala  Asn  Gly  Asp  Asn  Ala  Met  Ala  Ser  Val  Phe  Leu  Ser  Ile  Gln
205                      210                 215                      220

TCG  GAC  GAG  GCC  AGG  CAC  ATG  GCC  AAC  GGG  TAC  GGC  TCG  GTC  ATG  GCG      3007
Ser  Asp  Glu  Ala  Arg  His  Met  Ala  Asn  Gly  Tyr  Gly  Ser  Val  Met  Ala
                    225                 230                      235

CTG  CTG  GAG  AAC  GAG  GAC  AAC  CTC  CCG  CTG  CTC  AAC  CAG  TCT  CTC  GAT      3055
Leu  Leu  Glu  Asn  Glu  Asp  Asn  Leu  Pro  Leu  Leu  Asn  Gln  Ser  Leu  Asp
               240                 245                      250

CGG  CAC  TTC  TGG  CGT  GCC  CAC  AAG  GCC  TTG  GAC  AAC  GCG  GTC  GGA  TCG      3103
Arg  His  Phe  Trp  Arg  Ala  His  Lys  Ala  Leu  Asp  Asn  Ala  Val  Gly  Ser
          255                 260                 265

TGT  TCG  GAG  TAT  GGC  GCC  CGC  AAG  CGG  CCA  TGG  AGC  TAC  AAG  GCC  CAG      3151
Cys  Ser  Glu  Tyr  Gly  Ala  Arg  Lys  Arg  Pro  Trp  Ser  Tyr  Lys  Ala  Gln
     270                      275                 280

TGG  GAG  GAA  TGG  GTC  GTC  GAC  GAC  TTC  GTG  GGC  GGC  TAC  ATC  GAC  CGA      3199
Trp  Glu  Glu  Trp  Val  Val  Asp  Asp  Phe  Val  Gly  Gly  Tyr  Ile  Asp  Arg
285                 290                 295                      300

CTC  AGC  GAG  TTC  GGC  GTT  CAG  GCT  CCG  GCC  TGC  CTT  GGC  GCG  GCC  GCC      3247
Leu  Ser  Glu  Phe  Gly  Val  Gln  Ala  Pro  Ala  Cys  Leu  Gly  Ala  Ala  Ala
                    305                 310                 315

GAC  GAG  GTC  AAG  TGG  TCG  CAC  CAC  ACC  CTC  GGT  CAG  GTG  CTG  TCG  GCG      3295
Asp  Glu  Val  Lys  Trp  Ser  His  His  Thr  Leu  Gly  Gln  Val  Leu  Ser  Ala
               320                 325                 330

GTG  TGG  CCG  CTG  AAC  TTC  TGG  CGC  TCG  GAC  GCC  ATG  GGA  CCG  GCG  GAC      3343
Val  Trp  Pro  Leu  Asn  Phe  Trp  Arg  Ser  Asp  Ala  Met  Gly  Pro  Ala  Asp
          335                 340                 345

TTC  GAG  TGG  TTC  GAG  AAC  CAC  TAC  CCG  GGC  TGG  AGC  GCG  GCC  TAC  CAG      3391
Phe  Glu  Trp  Phe  Glu  Asn  His  Tyr  Pro  Gly  Trp  Ser  Ala  Ala  Tyr  Gln
     350                      355                 360

GGT  TAC  TGG  GAG  GGC  TAC  AAG  GCG  CTC  GCC  GAC  CCA  GCA  GGC  GGA  CGC      3439
Gly  Tyr  Trp  Glu  Gly  Tyr  Lys  Ala  Leu  Ala  Asp  Pro  Ala  Gly  Gly  Arg
365                 370                 375                      380

ATC  ATG  CTC  CAG  GAG  CTG  CCG  GGT  CTG  CCG  CCG  ATG  TGT  CAG  GTG  TGC      3487
Ile  Met  Leu  Gln  Glu  Leu  Pro  Gly  Leu  Pro  Pro  Met  Cys  Gln  Val  Cys
                    385                 390                 395

CAG  GTG  CCG  TGC  GTG  ATG  CCG  CGG  CTG  GAT  ATG  AAC  GCC  GCG  CGG  ATC      3535
Gln  Val  Pro  Cys  Val  Met  Pro  Arg  Leu  Asp  Met  Asn  Ala  Ala  Arg  Ile
               400                 405                 410

ATC  GAG  TTC  GAG  GGG  CAG  AAA  ATC  GCG  CTG  TGC  AGC  GAA  CCC  TGC  CAG      3583
Ile  Glu  Phe  Glu  Gly  Gln  Lys  Ile  Ala  Leu  Cys  Ser  Glu  Pro  Cys  Gln
          415                 420                 425

CGG  ATC  TTC  ACC  AAC  TGG  CCG  GAG  GCG  TAC  CGC  CAC  CGC  AAG  CAA  TAC      3631
Arg  Ile  Phe  Thr  Asn  Trp  Pro  Glu  Ala  Tyr  Arg  His  Arg  Lys  Gln  Tyr
     430                      435                 440

TGG  GCC  CGC  TAC  CAC  GGA  TGG  GAC  CTG  GCG  GAC  GTC  ATC  GTT  GAT  CTC      3679
Trp  Ala  Arg  Tyr  His  Gly  Trp  Asp  Leu  Ala  Asp  Val  Ile  Val  Asp  Leu
445                 450                 455                      460

GGC  TAC  ATC  CGC  CCG  GAC  GGC  AAG  ACC  CTC  ATC  GGC  CAG  CCG  CTG  CTC      3727
Gly  Tyr  Ile  Arg  Pro  Asp  Gly  Lys  Thr  Leu  Ile  Gly  Gln  Pro  Leu  Leu
                    465                 470                 475

GAG  ATG  GAG  CGG  CTG  TGG  ACC  ATC  GAC  GAC  ATC  CGG  GCC  CTT  CAG  TAC      3775
Glu  Met  Glu  Arg  Leu  Trp  Thr  Ile  Asp  Asp  Ile  Arg  Ala  Leu  Gln  Tyr
               480                 485                 490

GAA  GTC  AAG  GAC  CCG  TTG  CAG  GAG  GCG  TG   ATG  ACG  ACG  ATC  AAT  GTG      3822
```

|                                                                                      |      |
|---|---|
| Glu Val Lys Asp Pro Leu Gln Glu   Met Thr Thr Ile Asn Val<br>    495         500     1             5                                     |      |
| CAG CCC TTC TCA CAC GAG TAC TCG TGC GAG GAC GGC GAG AGC CTC CTC<br>Gln Pro Phe Ser His Glu Tyr Ser Cys Glu Asp Gly Glu Ser Leu Leu<br>         10              15              20             | 3870 |
| GAC GGC GCC CTG CGC AAC AGC CTC CTC AAG TAC GGG TGC AAG CAC<br>Asp Gly Ala Leu Arg Asn Ser Leu Leu Leu Lys Tyr Gly Cys Lys His<br>     25              30              35 | 3918 |
| GGG GGC TGC GGG ACC TGC AAG GTC CGG CTG CTC GAC GGC GAC GTA GAG<br>Gly Gly Cys Gly Thr Cys Lys Val Arg Leu Leu Asp Gly Asp Val Glu<br>    40              45              50 | 3966 |
| GAA CCC GGG TCG TCG TTC GCG CTG ACG CCG GAG GAC CGC GAG AAC GAC<br>Glu Pro Gly Ser Ser Phe Ala Leu Thr Pro Glu Asp Arg Glu Asn Asp<br>55              60              65              70 | 4014 |
| GTG ATC CTC GCG TGC GCC AGC GTG CCG CTG GAA CCG TGC ACC ATC GAC<br>Val Ile Leu Ala Cys Ala Ser Val Pro Leu Glu Pro Cys Thr Ile Asp<br>            75              80              85 | 4062 |
| GTC GAG CCG AGC GGC CTC ACG GAG GAG GAG TTC TTC TCG GGC GAC ACC<br>Val Glu Pro Ser Gly Leu Thr Glu Glu Glu Phe Phe Ser Gly Asp Thr<br>    90              95             100 | 4110 |
| TCG CGC GAG TTC CAG ACG GTC GTG GGC GGT GTC GAG TTT CTC ACG GCG<br>Ser Arg Glu Phe Gln Thr Val Val Gly Gly Val Glu Phe Leu Thr Ala<br>        105             110             115 | 4158 |
| GAC ATC GCC CGG GTC CGG CTC CGG CTA GAG CCG GGC GAG GAG ATC GCC<br>Asp Ile Ala Arg Val Arg Leu Arg Leu Glu Pro Gly Glu Glu Ile Ala<br>    120             125             130 | 4206 |
| TTC ACC GCC GGT CAG TTC GTC AAC GTC GAG GTG CCG GGC ACG GGT CTG<br>Phe Thr Ala Gly Gln Phe Val Asn Val Glu Val Pro Gly Thr Gly Leu<br>135             140             145             150 | 4254 |
| CTG CGG ACC TTC TCG CTG GCA AAC GCC CCT GAC GAC CCG TCA GTG GTG<br>Leu Arg Thr Phe Ser Leu Ala Asn Ala Pro Asp Asp Pro Ser Val Val<br>            155             160             165 | 4302 |
| GAG CTG ATC TGC AAG CTC TAC CCG GAT GGC CTC TTC TCC CGC TTC CTG<br>Glu Leu Ile Cys Lys Leu Tyr Pro Asp Gly Leu Phe Ser Arg Phe Leu<br>        170             175             180 | 4350 |
| AGG GAC GAG GCT GCC CCG GGC ACG CCG GTC CGG GTG TTC GGG CCG TAT<br>Arg Asp Glu Ala Ala Pro Gly Thr Pro Val Arg Val Phe Gly Pro Tyr<br>    185             190             195 | 4398 |
| GGT CAG CTC AAG ATC CGC TTG TCC CAC CGG CCG ATC CTG ATG ATC GCC<br>Gly Gln Leu Lys Ile Arg Leu Ser His Arg Pro Ile Leu Met Ile Ala<br>200             205             210 | 4446 |
| GGT GGG TCC GGT CTC GCC CCG CTG CTC TCG ATG CTG CGA GAC TTG GCC<br>Gly Gly Ser Gly Leu Ala Pro Leu Leu Ser Met Leu Arg Asp Leu Ala<br>215             220             225             230 | 4494 |
| GCC AAG AAG TGC GAC CGG CCG GTC TCG ATG TTC TTC GGC GCA CGC AGC<br>Ala Lys Lys Cys Asp Arg Pro Val Ser Met Phe Phe Gly Ala Arg Ser<br>            235             240             245 | 4542 |
| GTC GAC GAC CTG TAC CTC ATC GAG GAG ATC CGC GAG ATC GGC GAG TCG<br>Val Asp Asp Leu Tyr Leu Ile Glu Glu Ile Arg Glu Ile Gly Glu Ser<br>        250             255             260 | 4590 |
| CTA GCC GAT TTC GAG TTC ATC CCC GTG CTC TCG GAG TCG TCG CCA GCC<br>Leu Ala Asp Phe Glu Phe Ile Pro Val Leu Ser Glu Ser Ser Pro Ala<br>    265             270             275 | 4638 |
| GAC TGG CAC GGC GAG ACG GGC ATG GTC ACC GAC GCC TTG CTG CGG TGG<br>Asp Trp His Gly Glu Thr Gly Met Val Thr Asp Ala Leu Leu Arg Trp<br>280             285             290 | 4686 |
| CGC GCC GAA CTG GCG CAT GAC GTC TAC CTG TGC GGG CCG CCA CCC ATG<br>Arg Ala Glu Leu Ala His Asp Val Tyr Leu Cys Gly Pro Pro Pro Met<br>295             300             305             310 | 4734 |
| ATC GAC GCC GCT GTG CCG CTG CTC GTC GAG CGG GGC GTG CGC CCA CGC | 4782 |

```
Ile Asp Ala Ala  Val  Pro  Leu  Leu  Val  Glu  Arg  Gly  Val  Arg  Pro  Arg
            315                      320                      325

AAC ATC TAC TAC GAC GCA TTC ACC CCA GCT GCT CAG GTA GTC GTC GTC           4830
Asn Ile Tyr Tyr Asp Ala Phe Thr Pro Ala Ala Gln Val Val Val Val
            330                      335                      340

TGATGGTGCA TATCCGATTG GGCGGCCGGT ACCGGCGGGG TTAGGGCAGG GTAATCGGCC          4890
GCGATAGAGG CAGCCAGCAG AGATGATGCG CGTGCAAAGC GAAGCTTCGA CTCAGTTGAC          4950
ACCTTCGGCA ATGTGCTGTG CGAGCACGAT AACCGTGTGT TACGGGTGAG GCTCAATCGC          5010
ACCGGTGCCC TGAGCGCAAT CAATTCAGCT ATGGCTGATC AATTGCGGGA AGCGTGGGTG          5070
TGGGTGCGCA GCCAAACCGG AATTCATTCA ATCGTCATCT CGGCTTCGCG GCCGGAGTCG          5130
TTTTTGCATC GGTTTTGATC CGGCCGACCC GCCGGAGCCG ATGTTCGATC GCCCCATCAG          5190
CCCGAAGGAA TGCGGCGTCG ATCAACGCGT CATAGTCGCG GTGAACGGCA TCGCGTGCCG          5250
CATCCTGAGC GCCGGCGAAC CGACACTGCG TAAGCCGGTG ACGGCGGAAC AGGCGATGGA          5310
GTCGGGCTTG GTTCGGGAGG TCGTACCGCT TGCATCGGCT GCGTTGTCGA GCGAATAGCT          5370
CAGGCGGCAG GACATCGTAT AGGGATTCAG GTGGGTAGTT GATCTTCCGC GTGTCGATGT          5430
GTGACGGGCC GGATCTGGCC TACGAACAAC ATCAGCAAGC GTGACCTTCG GCCCACAACA          5490
TCGTGCCGTC CGCGACCGGT GCCGACCGTG ATCTCGGCGA AGTCCTGCCG GAGTTCGCGG          5550
GGCGGTTCCA CAGCGTTGGG GGTCCCTCGG CTACACCTCG GCGCTGTTCG TCAGCTCCGA          5610
CATCATCGGT CACCCACACT CCTGCCCGGT GTTCGGCAAC ATGGTGCACG ACGGCCAGGT          5670
GAACCTTCGG CTGGTACGAC AACGAATGGG CGATGCCAAT CCGTTGCTCG ACCTCGTCGG          5730
GGTCATGGCT GGCGTTCGCT GACTAGGCGG CCTGTTCGTG CCGGCCGCAA CATCCAGCCC          5790
GTGAGGAGTT GCGTACCGGT CGGCGAGAAA CTCCACGACC CGGGCAACCT CGTCGGGCTC          5850
ACCGAGTCGG CCGACTGGGA TCTTCGCGAT GACCCGATCG AGCGCCTCCT TGGGCACCGC          5910
AGCAACTATC TCGGTGGAGA TGTAGCCAGG CGGAACGGAA TTGACGGTGA TGCCCTTGCG          5970
GGCGGTCTCC TGGGCCAGGG TCTGTGTCCT TATCTCTTGT CGACCGAACA CGGTGTGCGG          6030
TCGAGTTGGT CGGTTTGATC AGGCGGGAAC GCGGAATAGG AGGGCTTCGC CCTGACCGCC          6090
GCCGCCGCAC AGGCCGGCCG CCCCGACGCC GCCGCCGCGG CGGGCCAGCT CGAGCACGAG          6150
ATGCAGCGCG ATCCGGGCGC CGGAGGCGCC GACCGGGTGC CCCATGGCGA TCGCGCCGCC          6210
GTTGACGTTG ACGTTGTCGG GGCCGATCTG CAGGTCGCGC ATGGATTGAA TAGCGACGGC          6270
CGCGAATGCC TCGTTGATCT CGTACAGGTC CACATCCATG GCGGAGAGTC CTTCGCGGCG          6330
CAGCGCCCTG GCGATCGCGT TGGAGGGTTG CGACAGCAGC GAGGGATCC                     6379
```

( 2 ) INFORMATION FOR SEQ ID NO:2:

( i ) SEQUENCE CHARACTERISTICS:
        ( A ) LENGTH: 342 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Thr Thr Glu Ala Thr  Val  Ala  Arg  Pro  Val  Glu  Leu  Glu  Gly  His  Arg
  1           5                      10                       15

Thr Phe Thr Trp Phe  Thr  Pro  Ala  Arg  Arg  Lys  Pro  Thr  Glu  Tyr  Glu
            20                       25                       30

Leu Tyr Thr Val Gly  Gln  Gln  Ser  Thr  Pro  Asp  Glu  Trp  Leu  His  Val
        35                       40                       45
```

Asp Trp Pro Leu Arg Phe Asp Asp Gly Arg Ala Pro Trp Glu Glu Glu
            50                      55                      60

Ser Ser Ala Val Arg Thr Ser Glu Trp Ser Ala Tyr Arg Asp Pro His
65                      70                      75                      80

Gln Leu Trp Gln Arg Pro Tyr Val Ser Thr Cys Asn Gln Asp Gln Gln
                    85                      90                      95

Ala Leu Ala Arg Leu Val Pro Val Leu Thr Met Gly Ser Ala Ala Ile
                100                     105                     110

Thr Pro Ile Trp Ser Gln Lys Ile Leu Ala Arg Ser Tyr Ala Ala Trp
            115                     120                     125

Pro Phe Val Glu Tyr Gly Leu Phe Leu Ser Leu Ala Tyr Ala Val Arg
        130                     135                     140

Gln Ala Met Ser Asp Thr Val Gln Phe Ser Val Val Phe Gln Ala Val
145                     150                     155                     160

Asp Arg Met Arg Leu Leu Gln Asp Ile Val His His Leu Asp His Leu
                165                     170                     175

Gln Glu Ser Pro Glu Phe Ser Asp Ala Gly Ala Arg Glu Ala Trp Met
            180                     185                     190

Ser Asp Ser Thr Leu Val Pro Ile Arg Glu Val Ile Glu Arg Ile Ala
        195                     200                     205

Ala Ser Gln Asp Trp Val Glu Ile Leu Val Ala Gly Thr Leu Val Phe
210                     215                     220

Glu Pro Leu Val Gly His Leu Ala Lys Ala Glu Leu Phe Ser Arg Arg
225                     230                     235                     240

Ala Pro Met Phe Gly Asp Gly Thr Pro Pro Ala Val Leu Ala Ser Ala
                245                     250                     255

Leu Leu Asp Ser Gly Arg His Leu Glu Ser Val Gln Ala Leu Val Arg
            260                     265                     270

Leu Val Cys Gln Asp Pro Val His Gly Asp Gln Asn Gln Ala Thr Val
        275                     280                     285

Arg Arg Trp Ile Glu Glu Trp Gln Pro Arg Cys Lys Ala Ala Ala Gln
290                     295                     300

Ser Phe Leu Pro Thr Phe Ser Asp Cys Gly Ile Asp Ala Lys Glu Ser
305                     310                     315                     320

Ala Asn Ala Leu Ser Arg Ala Leu Ala Asn Gln Arg Ala Ala Val Glu
                325                     330                     335

Gly Ala Gly Ile Thr Ala
            340

( 2 ) INFORMATION FOR SEQ ID NO:3:

( i ) SEQUENCE CHARACTERISTICS:
        ( A ) LENGTH: 117 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

Met Thr Asp Val Lys Glu Thr Thr Val Thr Ser Thr Pro Ser Ala Ala
1                   5                       10                      15

Val Pro Gly Thr Lys Asn Arg Arg Val Gly Ile Ser Leu Ile Ser Ser
            20                      25                      30

Ser Asp Thr Glu Ala Ala Val Glu His Ile Ala Glu Thr Gln Pro Asp
        35                      40                      45

Ala Lys Ile Asp Phe Arg Asp Cys Phe Tyr Lys Ile Glu Arg Asp Gly
    50                      55                      60

Gln Leu Ser Phe Asp Met Ala Glu Leu Ser Glu Ile Ala Gly Arg Asp
65                  70                  75                  80

Ile Asp Thr Asp Ile Phe Leu Val Asn Met Ser Thr Tyr Tyr Gly Arg
                85                  90                  95

Ile Val Val Ser Asp Gly Arg Val Asp Ile Tyr Ala Glu Ile Gln Pro
                100                 105                 110

Ala Arg Phe Lys Asp
                115

(2) INFORMATION FOR SEQ ID NO:4:

(i) SEQUENCE CHARACTERISTICS:
        (A) LENGTH: 501 amino acids
        (B) TYPE: amino acid
        (D) TOPOLOGY: linear (ii) MOLECULE TYPE: protein (xi) SEQUENCE DESCRIPTION: SEQ ID NO:4:

Met Ala Ser Asn Pro Thr Gln Leu His Glu Lys Ser Lys Ser Tyr Asp
1                   5                   10                  15

Trp Asp Phe Thr Ser Val Glu Arg Arg Pro Lys Phe Glu Thr Lys Tyr
                20                  25                  30

Lys Met Pro Lys Lys Gly Lys Asp Pro Phe Arg Val Leu Ile Arg Asp
                35                  40                  45

Tyr Met Lys Met Glu Ala Glu Lys Asp Asp Arg Thr His Gly Phe Leu
    50                  55                  60

Asp Gly Ala Val Arg Thr Arg Glu Ala Thr Arg Ile Glu Pro Arg Phe
65                  70                  75                  80

Ala Glu Ala Met Lys Ile Met Val Pro Gln Leu Thr Asn Ala Glu Tyr
                85                  90                  95

Gln Ala Val Ala Gly Cys Gly Met Ile Ile Ser Ala Val Glu Asn Gln
                100                 105                 110

Glu Leu Arg Gln Gly Tyr Ala Ala Gln Met Leu Asp Glu Val Arg His
                115                 120                 125

Ala Gln Leu Glu Met Thr Leu Arg Asn Tyr Tyr Ala Lys His Trp Cys
    130                 135                 140

Asp Pro Ser Gly Phe Asp Ile Gly Gln Arg Gly Leu Tyr Gln His Pro
145                 150                 155                 160

Ala Gly Leu Val Ser Ile Gly Glu Phe Gln His Phe Asn Thr Gly Asp
                165                 170                 175

Pro Leu Asp Val Ile Ile Asp Leu Asn Ile Val Ala Glu Thr Ala Phe
                180                 185                 190

Thr Asn Ile Leu Leu Val Ala Thr Pro Gln Val Ala Val Ala Asn Gly
        195                 200                 205

Asp Asn Ala Met Ala Ser Val Phe Leu Ser Ile Gln Ser Asp Glu Ala
210                 215                 220

Arg His Met Ala Asn Gly Tyr Gly Ser Val Met Ala Leu Leu Glu Asn
225                 230                 235                 240

Glu Asp Asn Leu Pro Leu Leu Asn Gln Ser Leu Asp Arg His Phe Trp
                245                 250                 255

Arg Ala His Lys Ala Leu Asp Asn Ala Val Gly Ser Cys Ser Glu Tyr
                260                 265                 270

Gly Ala Arg Lys Arg Pro Trp Ser Tyr Lys Ala Gln Trp Glu Glu Trp
                275                 280                 285

Val Val Asp Asp Phe Val Gly Gly Tyr Ile Asp Arg Leu Ser Glu Phe

```
                290                     295                     300
Gly  Val  Gln  Ala  Pro  Ala  Cys  Leu  Gly  Ala  Ala  Ala  Asp  Glu  Val  Lys
305                     310                     315                     320

Trp  Ser  His  His  Thr  Leu  Gly  Gln  Val  Leu  Ser  Ala  Val  Trp  Pro  Leu
                    325                     330                     335

Asn  Phe  Trp  Arg  Ser  Asp  Ala  Met  Gly  Pro  Ala  Asp  Phe  Glu  Trp  Phe
                340                     345                     350

Glu  Asn  His  Tyr  Pro  Gly  Trp  Ser  Ala  Ala  Tyr  Gln  Gly  Tyr  Trp  Glu
               355                     360                     365

Gly  Tyr  Lys  Ala  Leu  Ala  Asp  Pro  Ala  Gly  Gly  Arg  Ile  Met  Leu  Gln
          370                     375                     380

Glu  Leu  Pro  Gly  Leu  Pro  Pro  Met  Cys  Gln  Val  Cys  Gln  Val  Pro  Cys
385                     390                     395                     400

Val  Met  Pro  Arg  Leu  Asp  Met  Asn  Ala  Ala  Arg  Ile  Ile  Glu  Phe  Glu
                405                     410                     415

Gly  Gln  Lys  Ile  Ala  Leu  Cys  Ser  Glu  Pro  Cys  Gln  Arg  Ile  Phe  Thr
                420                     425                     430

Asn  Trp  Pro  Glu  Ala  Tyr  Arg  His  Arg  Lys  Gln  Tyr  Trp  Ala  Arg  Tyr
          435                     440                     445

His  Gly  Trp  Asp  Leu  Ala  Asp  Val  Ile  Val  Asp  Leu  Gly  Tyr  Ile  Arg
     450                     455                     460

Pro  Asp  Gly  Lys  Thr  Leu  Ile  Gly  Gln  Pro  Leu  Leu  Glu  Met  Glu  Arg
465                     470                     475                     480

Leu  Trp  Thr  Ile  Asp  Asp  Ile  Arg  Ala  Leu  Gln  Tyr  Glu  Val  Lys  Asp
               485                     490                     495

Pro  Leu  Gln  Glu  Ala
               500

( 2 ) INFORMATION FOR SEQ ID NO:5:

( i ) SEQUENCE CHARACTERISTICS:
                ( A ) LENGTH: 342 amino acids
                ( B ) TYPE: amino acid
                ( D ) TOPOLOGY: linear ( i i ) MOLECULE TYPE: protein ( x i ) SEQUENCE DESCRIPTION: SEQ ID NO:5:

Met  Thr  Thr  Ile  Asn  Val  Gln  Pro  Phe  Ser  His  Glu  Tyr  Ser  Cys  Glu
1                   5                       10                      15

Asp  Gly  Glu  Ser  Leu  Leu  Asp  Gly  Ala  Leu  Arg  Asn  Ser  Leu  Leu  Leu
               20                      25                      30

Lys  Tyr  Gly  Cys  Lys  His  Gly  Gly  Cys  Gly  Thr  Cys  Lys  Val  Arg  Leu
          35                      40                      45

Leu  Asp  Gly  Asp  Val  Glu  Glu  Pro  Gly  Ser  Ser  Phe  Ala  Leu  Thr  Pro
     50                      55                      60

Glu  Asp  Arg  Glu  Asn  Asp  Val  Ile  Leu  Ala  Cys  Ala  Ser  Val  Pro  Leu
65                      70                      75                      80

Glu  Pro  Cys  Thr  Ile  Asp  Val  Glu  Pro  Ser  Gly  Leu  Thr  Glu  Glu  Glu
               85                      90                      95

Phe  Phe  Ser  Gly  Asp  Thr  Ser  Arg  Glu  Phe  Gln  Thr  Val  Val  Gly  Gly
               100                     105                     110

Val  Glu  Phe  Leu  Thr  Ala  Asp  Ile  Ala  Arg  Val  Arg  Leu  Arg  Leu  Glu
          115                     120                     125

Pro  Gly  Glu  Glu  Ile  Ala  Phe  Thr  Ala  Gly  Gln  Phe  Val  Asn  Val  Glu
     130                     135                     140
```

| | | | | | | | | | | | | | | | |
|---|---|---|---|---|---|---|---|---|---|---|---|---|---|---|---|
| Val 145 | Pro | Gly | Thr | Gly | Leu 150 | Leu | Arg | Thr | Phe | Ser 155 | Leu | Ala | Asn | Ala | Pro 160 |
| Asp | Asp | Pro | Ser | Val 165 | Val | Glu | Leu | Ile | Cys 170 | Lys | Leu | Tyr | Pro | Asp 175 | Gly |
| Leu | Phe | Ser | Arg 180 | Phe | Leu | Arg | Asp | Glu 185 | Ala | Ala | Pro | Gly | Thr 190 | Pro | Val |
| Arg | Val | Phe 195 | Gly | Pro | Tyr | Gly | Gln 200 | Leu | Lys | Ile | Arg | Leu 205 | Ser | His | Arg |
| Pro | Ile 210 | Leu | Met | Ile | Ala | Gly 215 | Gly | Ser | Gly | Leu | Ala 220 | Pro | Leu | Leu | Ser |
| Met 225 | Leu | Arg | Asp | Leu | Ala 230 | Ala | Lys | Lys | Cys | Asp 235 | Arg | Pro | Val | Ser | Met 240 |
| Phe | Phe | Gly | Ala | Arg 245 | Ser | Val | Asp | Asp | Leu 250 | Tyr | Leu | Ile | Glu | Glu 255 | Ile |
| Arg | Glu | Ile | Gly 260 | Glu | Ser | Leu | Ala | Asp 265 | Phe | Glu | Phe | Ile | Pro 270 | Val | Leu |
| Ser | Glu | Ser 275 | Ser | Pro | Ala | Asp | Trp 280 | His | Gly | Glu | Thr | Gly 285 | Met | Val | Thr |
| Asp | Ala 290 | Leu | Leu | Arg | Trp | Arg 295 | Ala | Glu | Leu | Ala | His 300 | Asp | Val | Tyr | Leu |
| Cys 305 | Gly | Pro | Pro | Pro | Met 310 | Ile | Asp | Ala | Ala | Val 315 | Pro | Leu | Leu | Val | Glu 320 |
| Arg | Gly | Val | Arg | Pro 325 | Arg | Asn | Ile | Tyr | Tyr 330 | Asp | Ala | Phe | Thr | Pro 335 | Ala |
| Ala | Gln | Val | Val 340 | Val | Val | | | | | | | | | | |